(12) United States Patent
Cao et al.

(10) Patent No.: US 11,103,588 B2
(45) Date of Patent: Aug. 31, 2021

(54) METHODS AND COMPOSITIONS RELATING TO CARNITINE-DERIVED MATERIALS

(71) Applicant: Wayne State University, Detroit, MI (US)

(72) Inventors: Zhiqiang Cao, Troy, MI (US); Wei Wang, Schaumburg, IL (US); Yang Lu, Shanghai (CN)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 16/619,806

(22) PCT Filed: Jun. 6, 2018

(86) PCT No.: PCT/US2018/036271
§ 371 (c)(1),
(2) Date: Dec. 5, 2019

(87) PCT Pub. No.: WO2018/226841
PCT Pub. Date: Dec. 13, 2018

(65) Prior Publication Data
US 2020/0129628 A1 Apr. 30, 2020

Related U.S. Application Data

(60) Provisional application No. 62/623,844, filed on Jan. 30, 2018, provisional application No. 62/573,431, filed on Oct. 17, 2017, provisional application No. 62/515,704, filed on Jun. 6, 2017.

(51) Int. Cl.
| | | |
|---|---|---|
| A61K 47/58 | (2017.01) | |
| C07C 229/22 | (2006.01) | |
| C07C 227/16 | (2006.01) | |
| A61K 47/69 | (2017.01) | |
| A61K 31/337 | (2006.01) | |
| A61K 47/54 | (2017.01) | |
| C08G 81/02 | (2006.01) | |
| A61K 38/28 | (2006.01) | |
| C08F 120/36 | (2006.01) | |
| A61K 39/00 | (2006.01) | |
| A61K 35/76 | (2015.01) | |
| A61K 39/39 | (2006.01) | |
| C12N 15/86 | (2006.01) | |

(52) U.S. Cl.
CPC ........... *A61K 47/58* (2017.08); *A61K 31/337* (2013.01); *A61K 35/76* (2013.01); *A61K 38/28* (2013.01); *A61K 39/001106* (2018.08); *A61K 39/39* (2013.01); *A61K 47/543* (2017.08); *A61K 47/544* (2017.08); *A61K 47/6909* (2017.08); *A61K 47/6915* (2017.08); *A61K 47/6921* (2017.08); *C07C 227/16* (2013.01); *C07C 229/22* (2013.01); *C08F 120/36* (2013.01); *C08G 81/027* (2013.01); *C12N 15/86* (2013.01)

(58) Field of Classification Search
None
See application file for complete search history.

(56) References Cited

U.S. PATENT DOCUMENTS

| | | |
|---|---|---|
| 5,562,646 A | 10/1996 | Goldman et al. |
| 5,858,746 A | 1/1999 | Hubbell et al. |
| 7,144,992 B2 | 12/2006 | Madhyastha |
| 2006/0153775 A1 | 7/2006 | Von Wronski et al. |
| 2011/0097277 A1 | 4/2011 | Jiang et al. |
| 2011/0160392 A1 | 6/2011 | Chang et al. |
| 2012/0183602 A1 | 7/2012 | Chen et al. |
| 2012/0322939 A1 | 12/2012 | Jiang et al. |
| 2013/0011363 A1 | 1/2013 | Jiang et al. |
| 2013/0131214 A1 | 5/2013 | Scales et al. |
| 2014/0271843 A1 | 9/2014 | Ma et al. |
| 2016/0251470 A1 | 9/2016 | Cheng et al. |
| 2017/0231940 A1 | 8/2017 | Shah et al. |

FOREIGN PATENT DOCUMENTS

| | | | | |
|---|---|---|---|---|
| CN | 102697755 A | | 10/2012 | |
| CN | 105209562 A | | 12/2015 | |
| CN | 107519496 A | * | 12/2017 | ............ A61K 47/18 |
| EP | 0162764 A1 | | 11/1985 | |
| GB | 2071091 A | | 9/1981 | |
| JP | 2017026791 A | | 2/2017 | |
| KR | 1020150107156 A | * | 9/2015 | ............ G03F 7/004 |
| WO | WO-2000/61543 A2 | | 10/2000 | |
| WO | WO-2011/057225 A2 | | 5/2011 | |
| WO | WO-2012/024233 A2 | | 2/2012 | |
| WO | WO-2013/119183 A1 | | 8/2013 | |

OTHER PUBLICATIONS

Nurkeev A, Z. et al., Synthesis of Cationic Water-Soluble Copolymers and Hydrogels Based on [2-Methacryloyloxy)ethyl]trimethyammonium Chloride and 2-Hydroxyethylacrylate and Their Complex Formation with Poly(acrylic acid) Journal of Polymer Science: Part B: Polymer Physics, 44: 845-853, 2006.

Kou, L. et al., Dual targeting of L-carnitine-conjugated nanoparticles to OCTN2 and $ATB^{0,+}$ to deliver chemtherapeutic agents for colon cancer therapy, Drug Delivery, 24(1):1338-1349, 2017.

Wang, W. et al., Superdurable Coating Fabricated from a Double-Sided Tape with Long Term "Zero" Bacterial Adhesion, Adv. Mater. 29: 1606506, 2017.

Zhang, L. et al., Zwitterionic hydrogels implanted in mice resist the foreign body reaction, Nature Biotechnology, 31(6): 553-556, May 12, 2013.

(Continued)

*Primary Examiner* — Brian J Davis
(74) *Attorney, Agent, or Firm* — Julie K. Staple; Dinsmore & Shohl LLP

(57) ABSTRACT

Zwitterionic monomers, carnitine-derived zwitterionic polymers, carnitine ester cationic monomers, carnitine ester cationic polymers, conjugate compositions including a carnitine-derived zwitterionic polymer, and related compositions' and methods are provided which have various uses including as coatings, pharmaceuticals, diagnostics, encapsulation materials, and antifouling materials, among other utilities.

27 Claims, 7 Drawing Sheets

(56) References Cited

OTHER PUBLICATIONS

Chien, H. et al., Direct cell encapsulation in biodegradable and functionalizable carboxybetaine hydrogels, Biomaterials, 33(23): 5706-5712, Apr. 11, 2012.
Lin, C. et al., Peptide-Modified Zwitterionic Porous Hydrogels for Endothelial Cell and Vascular Engineering, Bio Research Open Access, 3(6): 297-310, Dec. 2014.
Wang, L. et al., Development of a Protein Mimic with Peptide Ligands to Enhane Specific Sensing and Targeting by the Zwitterionic Surface Engineering of Poly(amido amine) Dendrimers, Advanced Materials Interfaces, 1(1): 1300059, Feb. 1, 2014.

* cited by examiner

METHODS AND COMPOSITIONS RELATING TO CARNITINE-DERIVED MATERIALS

REFERENCE TO RELATED APPLICATIONS

This application claims priority from U.S. Provisional Patent Application Ser. Nos. 62/515,704, filed Jun. 6, 2017; 62/573,431, filed Oct. 17, 2017; and 62/623,844, filed Jan. 30, 2018. The entire content of each application is incorporated herein by reference.

GRANT REFERENCE

This invention was made with government support under Grant No. DMR1410853, awarded by the NSF and Grant No. DP2DK111910, awarded by the NIH. The Government has certain rights in the invention.

FIELD OF THE INVENTION

According to general aspects, carnitine-derived monomers and polymers are provided, along with methods of their synthesis. According to specific aspects, L-carnitine-derived monomers and polymers are provided, along with methods of their synthesis.

BACKGROUND OF THE INVENTION

Zwitterionic materials, such as poly-carboxybetaine (PCB), poly-sulfobetaine (PSB) and poly-phosphorylcholine (PPC), have been intensely studied for applications in the fields of biomedical devices and marine coating industry as an effective anti-fouling strategy to avoid protein binding and microorganism adhesion. Currently, most of these betaine polymers or monomers are synthesized from petrochemical derivatives. As global fossil fuel dwindles, there is a continuing need for methods and compositions relating to zwitterionic materials produced from natural feedstock, such as carnitine-derived zwitterionic materials and L-carnitine-derived zwitterionic materials.

SUMMARY OF THE INVENTION

Carnitine-derived zwitterionic monomers having the structural formula (I):

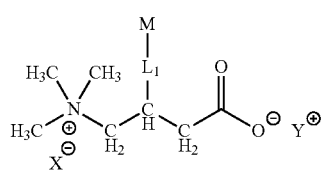

(I)

are provided according to aspects of the present invention, where M is a monomeric repeating unit, $L_1$ is a linker, X– is a counter ion associated with a cationic center of structure (I) and Y+ is a counter ion associated with an anionic center of structure (I). According to aspects of the present invention, M is a repeating unit of a polymer selected from the group consisting of: polyester, polyamide, poly(amino acid), polyimide, polycarbonate, polysiloxane, polyurethane, polyphosphazene, acrylic polymer, amino resin, epoxy resin, phenolic resin, and alkyd resin. According to aspects of the present invention, L1 is $-C(=O)O-(CH_2)_{n1}-$ or $-C(=O)NH-(CH_2)_{n1}-$, where n1 is an integer from 1 to 20, such as where n1 is 1, 2, 3, 4, 5, 6, 7, 8, 9, 10, 11, 12, 13, 14, 15, 16, 17, 18, 19, or 20.

Carnitine-derived zwitterionic monomers having the structural formula (II):

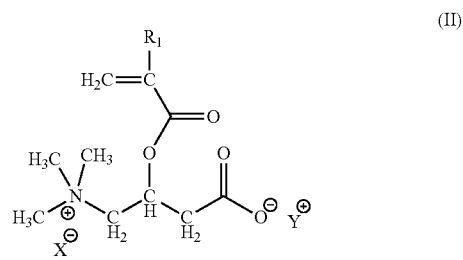

(II)

are provided according to aspects of the present invention, where $R_1$ is selected from the group consisting of: hydrogen, fluorine, trifluoromethyl, $C_1$-$C_6$ alkyl, and $C_6$-$C_{12}$ aryl groups, X– is a counter ion associated with the cationic center of structure (II) and Y+ is a counter ion associated with the anion center of structure (II).

Carnitine-derived zwitterionic monomers having the structural formula (IIa):

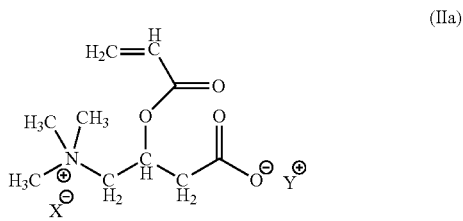

(IIa)

are provided according to aspects of the present invention, where X– is a counter ion associated with the cationic center of structure (IIa) and Y+ is a counter ion associated with the anion center of structure (IIa).

Carnitine-derived zwitterionic polymers having the structural formula (IV):

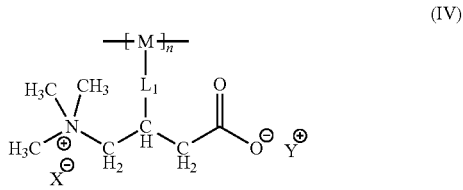

(IV)

are provided according to aspects of the present invention, where M is a monomeric repeating unit, $L_1$ is a linker, n is an integer from 1 to about 10000, X⁻ is a counter ion associated with the cationic center, and Y⁺ is a counter ion associated with the anionic center. According to aspects of the present invention, M is a repeating unit of a polymer selected from the group consisting of: polyester, polyamide, poly(amino acid), polyimide, polycarbonate, polysiloxane, polyurethane, polyphosphazene, acrylic polymer, amino resin, epoxy resin, phenolic resin, and alkyd resin.

According to aspects of the present invention, L1 is $-C(=O)O-(CH_2)_{n1}-$ or $-C(=O)NH-(CH_2)_{n1}-$, where n1 is an integer from 1 to 20, such as where n1 is 1, 2, 3, 4, 5, 6, 7, 8, 9, 10, 11, 12, 13, 14, 15, 16, 17, 18, 19, or 20.

Carnitine-derived zwitterionic polymers having the structural formula (V):

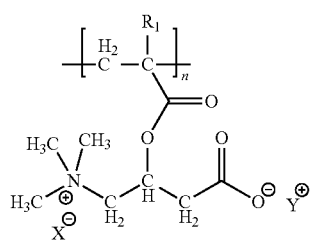
(V)

are provided according to aspects of the present invention, where $R_1$ is selected from the group consisting of hydrogen, fluorine, trifluoromethyl, $C_1$-$C_6$ alkyl, and $C_6$-$C_{12}$ aryl groups, n is an integer from 1 to about 10000, $X^-$ is a counter ion associated with the cationic center, and $Y^+$ is a counter ion associated with the anionic center.

Carnitine-derived zwitterionic polymers having the structural formula (Va):

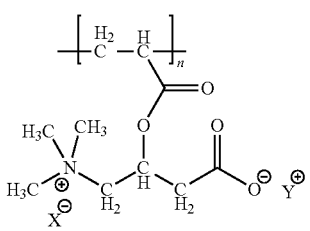
(Va)

are provided according to aspects of the present invention, where n is an integer from 1 to about 10000, $X^-$ is a counter ion associated with the cationic center, and $Y^+$ is a counter ion associated with the anionic center.

Carnitine ester cationic monomers having the structural formula (VII):

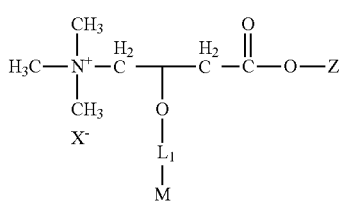
(VII)

are provided according to aspects of the present invention, where M is a monomeric repeating unit, $L_1$ is a linker, $X^-$ is a counter ion associated with the cationic center, and Z is an alkyl, aryl, acyl, silyl group, or a substituted alkyl, aryl, acyl, or silyl group.

Carnitine ester cationic monomers having the structural formula (VIII):

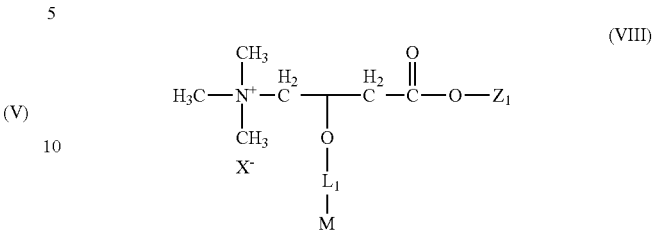
(VIII)

are provided according to aspects of the present invention, where M is a monomeric repeating unit, $L_1$ is a linker, $X^-$ is a counter ion associated with the cationic center, and $Z_1$ is a protecting group.

Carnitine ester cationic polymers having the structural formula (XVI):

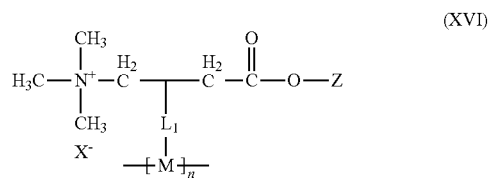
(XVI)

are provided according to aspects of the present invention, where M is a monomeric repeating unit, $L_1$ is a linker, n is an integer from 1 to about 10000, $X^-$ is a counter ion associated with the cationic center, and Z is an alkyl, aryl, acyl, silyl group, or a substituted alkyl, aryl, acyl, or silyl group.

Carnitine ester cationic polymers having the structural formula (XVI):

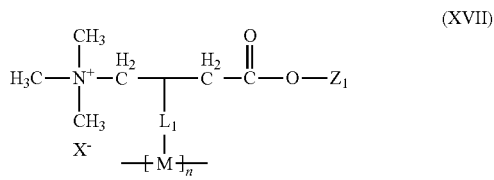
(XVII)

are provided according to aspects of the present invention, where M is a monomeric repeating unit, n is an integer from 1 to about 10000, $X^-$ is a counter ion associated with the cationic center, and $Z_1$ is a protecting group.

Conjugate compositions including a carnitine-derived zwitterionic polymer covalently coupled to a therapeutic and/or diagnostic agent are provided according to aspects of the present invention, wherein the carnitine-derived zwitterionic polymer has structural formula (IV), (V), or (Va).

Compositions including a carnitine-derived polymer wherein the polymer has structural formula (XXV):

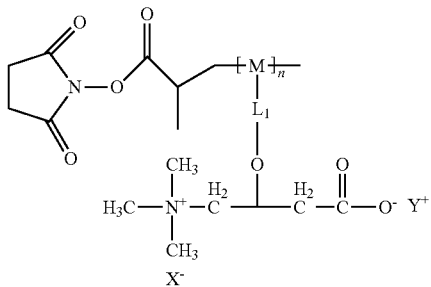

(XXV)

are provided according to aspects of the present invention, where M is a monomeric repeating unit, $L_1$ is a linker, n is an integer from 1 to about 10000, $X^-$ is a counter ion associated with the cationic center, and $Y^+$ is a counter ion associated with the anionic center.

Composition comprising a carnitine-derived polymer wherein the polymer has structural formula (XXVII):

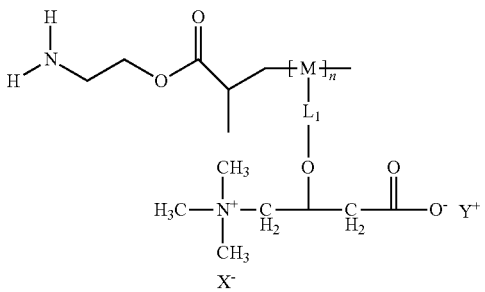

(XXVII)

are provided according to aspects of the present invention, where M is a monomeric repeating unit, $L_1$ is a linker, n is an integer from 1 to about 10000, $X^-$ is a counter ion associated with the cationic center, and $Y^+$ is a counter ion associated with the anionic center.

Conjugate compositions including a carnitine-derived zwitterionic polymer covalently coupled to a therapeutic and/or diagnostic agent by a degradable linkage between the polymer and the therapeutic or diagnostic agent are provided according to aspects of the present invention, wherein the carnitine-derived zwitterionic polymer has structural formula (IV), (V), or (Va). Optionally, the conjugate composition includes a pharmaceutically acceptable carrier or diluent.

Conjugate compositions including a carnitine-derived zwitterionic polymer covalently coupled to a therapeutic and/or diagnostic agent by a degradable linkage between the polymer and the therapeutic or diagnostic agent are provided according to aspects of the present invention, wherein the carnitine-derived zwitterionic polymer has structural formula (IV), (V), or (Va), and wherein the degradable linkage between the polymer and the therapeutic or diagnostic agent is degradable under certain conditions corresponding to conditions suitable for degradation of the specific linkage, examples of which are described herein, allowing the release of the agent in a particular environment. Optionally, the conjugate composition includes a pharmaceutically acceptable carrier or diluent.

Compositions including a plurality of conjugates including a carnitine-derived zwitterionic polymer covalently coupled to a therapeutic and/or diagnostic agent by a degradable linkage between the polymer and the therapeutic or diagnostic agent are provided according to aspects of the present invention, wherein the carnitine-derived zwitterionic polymer has structural formula (IV), (V), or (Va), and wherein the plurality of conjugates is associated to form an assembly, such as, but not limited to, a micelle or a particle. Optionally, the conjugate composition includes a pharmaceutically acceptable carrier or diluent.

Compositions including a plurality of conjugates including a carnitine-derived zwitterionic polymer covalently coupled to a therapeutic and/or diagnostic agent by a degradable linkage between the polymer and the therapeutic or diagnostic agent are provided according to aspects of the present invention, wherein the carnitine-derived zwitterionic polymer is covalently coupled to a therapeutic and/or diagnostic agent by a degradable linkage between the polymer and the therapeutic or diagnostic agent, wherein the carnitine-derived zwitterionic polymer has structural formula (IV), (V), or (Va), wherein the degradable linkage between the polymer and the therapeutic or diagnostic agent is degradable under certain conditions corresponding to conditions suitable for degradation of the specific linkage, examples of which are described herein, allowing the release of the agent in a particular environment, and wherein the plurality of conjugates is associated to form an assembly, such as, but not limited to, a micelle or a particle. Optionally, the conjugate composition includes a pharmaceutically acceptable carrier or diluent.

Conjugate compositions including a carnitine-derived zwitterionic polymer covalently coupled to a vesicle-forming lipid are provided according to aspects of the present invention, wherein the carnitine-derived zwitterionic polymer has the structural formula (IV). (V), or (Va). An assembly composition including a plurality of the conjugates is provided by the present invention. The assembly composition can be in the form of a micelle, a liposome, or a polymersome. According to aspects of the present invention, the assembly composition, such as a micelle, a liposome, or a polymersome, further includes a therapeutic and/or diagnostic agent. Optionally, the assembly composition includes a pharmaceutically acceptable carrier or diluent.

Conjugate compositions including a carnitine-derived zwitterionic polymer covalently coupled to a vesicle-forming lipid are provided according to aspects of the present invention, wherein the carnitine-derived zwitterionic polymer has the structural formula (IV), (V), or (Va), wherein the lipid is a phospholipid, a sphingolipid, or a sterol. An assembly composition including a plurality of the conjugates is provided by the present invention. The assembly composition can be in the form of a micelle, a liposome, or a polymersome. According to aspects of the present invention, the assembly composition, such as a micelle, a liposome, or a polymersome, further includes a therapeutic and/or diagnostic agent. Optionally, the assembly composition includes a pharmaceutically acceptable carrier or diluent.

Conjugate compositions including a carnitine-derived zwitterionic polymer covalently coupled to a vesicle-forming lipid are provided according to aspects of the present invention, wherein the carnitine-derived zwitterionic polymer has the structural formula (IV), (V), or (Va), wherein the lipid is a diacylphosphatidylethanolamine, a ceramide, a sphingomyelin, a dihydrosphingomyelin, a cephalin, or a cerebroside. An assembly composition including a plurality of the conjugates is provided by the present invention. The assembly composition can be in the form of a micelle, a liposome, or a polymersome. According to aspects of the present invention, the assembly composition, such as a micelle, a liposome, or a polymersome, further includes a therapeutic and/or diagnostic agent. Optionally, the assembly composition includes a pharmaceutically acceptable carrier or diluent.

Conjugate compositions including a carnitine-derived zwitterionic polymer covalently coupled to a vesicle-forming lipid are provided according to aspects of the present invention, wherein the carnitine-derived zwitterionic polymer has the structural formula (IV), wherein the lipid is distearoylphosphatidylethanolamine (DSEP), and wherein the conjugate composition has the structural formula (XXVI)

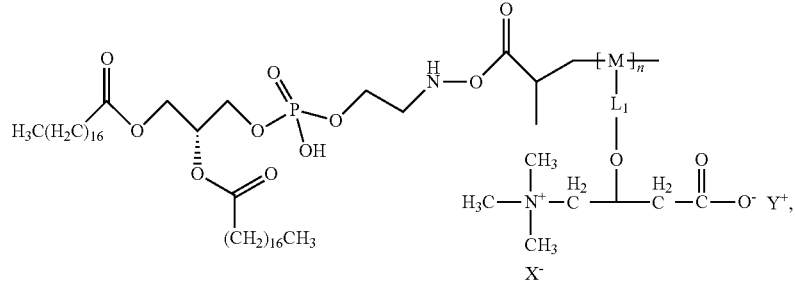

where M is a monomeric repeating unit, $L_1$ is a linker, n is an integer from 1 to about 10000, X− is a counter ion associated with the cationic center, and $Y^+$ is a counter ion associated with the anionic center. An assembly composition including a plurality of the conjugates is provided by the present invention. The assembly composition can be in the form of a micelle, a liposome, or a polymersome. According to aspects of the present invention, the assembly composition, such as a micelle, a liposome, or a polymersome, further includes a therapeutic and/or diagnostic agent. Optionally, the assembly composition includes a pharmaceutically acceptable carrier or diluent.

Conjugate compositions including a carnitine-derived zwitterionic polymer covalently coupled to a vesicle-forming lipid are provided according to aspects of the present invention, wherein the carnitine-derived zwitterionic polymer has the structural formula (IV), (V), or (Va), wherein the lipid is a phosphatidylethanolamine (PE), a phosphatidylglycerol (PG), aphosphatidic acid (PA), or a phosphatidylinositol (PI). An assembly composition including a plurality of the conjugates is provided by the present invention. The assembly composition can be in the form of a micelle, a liposome, or a polymersome. According to aspects of the present invention, the assembly composition, such as a micelle, a liposome, or a polymersome, further includes a therapeutic and/or diagnostic agent. Optionally, the assembly composition includes a pharmaceutically acceptable carrier or diluent.

Conjugate compositions including a carnitine-derived zwitterionic polymer covalently coupled to a vesicle-forming lipid are provided according to aspects of the present invention, wherein the carnitine-derived zwitterionic polymer has the structural formula (IV), (V), or (Va), wherein the lipid is selected from the group consisting of: dioleoylphosphatidylglycerol (DOPG), dipalmitoylphosphatidylglycerol (DPPG), dioleoyl-phosphatidylethanolamine (DOPE), palmitoyloleoyl-phosphatidylethanolamine (POPE), dipalmitoyl phosphatidyl ethanolamine (DPPE), dimyristoylphosphoethanolamine (DMPE), distearoyl-phosphatidylethanolamine (DSPE), 16-O-monomethyl-phosphoethanolamine, 16-O-dimethyl-phosphoethanolamine, 18-1-trans-phosphoethanolamine, 1-stearoyl-2-oleoyl-phosphatidyethanolamine (SOPE), 1,2-dioleoyl-sn-glycero-3-phophoethanolamine (transDOPE) and a combination of any two or more thereof. An assembly composition including a plurality of the conjugates is provided by the present invention. The assembly composition can be in the form of a micelle, a liposome, or a polymersome. According to aspects of the present invention, the assembly composition, such as a micelle, a liposome, or a polymersome, further includes a therapeutic and/or diagnostic agent. Optionally, the assembly composition includes a pharmaceutically acceptable carrier or diluent.

Diblock copolymers are provided according to aspects of the present invention which include: (a) a carnitine-derived zwitterionic polymer block according to structural formula (IV), and (b) a non-zwitterionic block. According to aspects of the present invention, the hydrophobic block has a number average molecular weight from about 1,000 to about 200,000. An assembly composition including a plurality of the diblock copolymers is provided by the present invention. The assembly composition can be in the form of a micelle, a particle, or a polymersome. According to aspects of the present invention, the assembly composition, such as a micelle, a particle, or a polymersome, further includes a therapeutic and/or diagnostic agent. Optionally, the assembly composition includes a pharmaceutically acceptable carrier or diluent.

Diblock copolymers are provided according to aspects of the present invention which include: (a) a carnitine-derived zwitterionic polymer block according to structural formula (IV), (V), or (Va), and (b) a non-zwitterionic block, wherein the non-zwitterionic block is a hydrophobic block. According to aspects of the present invention, the hydrophobic block has a number average molecular weight from about 1,000 to about 200,000. An assembly composition including a plurality of the diblock copolymers is provided by the present invention. The assembly composition can be in the form of a micelle, a particle, or a polymersome. According to aspects of the present invention, the assembly composition, such as a micelle, a particle, or a polymersome, further includes a therapeutic and/or diagnostic agent. Optionally, the assembly composition includes a pharmaceutically acceptable carrier or diluent.

Diblock copolymers are provided according to aspects of the present invention which include: (a) a carnitine-derived zwitterionic polymer block according to structural formula (IV), (V), or (Va), and (b) a non-zwitterionic block, wherein the non-zwitterionic block includes a homopolymer or copolymer. According to aspects of the present invention, the hydrophobic block has a number average molecular weight from about 1,000 to about 200,000. An assembly composition including a plurality of the diblock copolymers is provided by the present invention. The assembly composition can be in the form of a micelle, a particle, or a polymersome. According to aspects of the present invention, the assembly composition, such as a micelle, a particle, or a polymersome, further includes a therapeutic and/or diagnostic agent. Optionally, the assembly composition includes a pharmaceutically acceptable carrier or diluent.

Diblock copolymers are provided according to aspects of the present invention which include: (a) a carnitine-derived zwitterionic polymer block according to structural formula (IV), (V), or (Va), and (b) a non-zwitterionic block, wherein the non-zwitterionic block includes a biodegrable copolymer. According to aspects of the present invention, the hydrophobic block has a number average molecular weight from about 1,000 to about 200,000. An assembly composition including a plurality of the diblock copolymers is provided by the present invention. The assembly composition can be in the form of a micelle, a particle, or a polymersome. According to aspects of the present invention, the assembly composition, such as a micelle, a particle, or a polymersome, further includes a therapeutic and/or diagnostic agent. Optionally, the assembly composition includes a pharmaceutically acceptable carrier or diluent.

Diblock copolymers are provided according to aspects of the present invention which include: (a) a carnitine-derived zwitterionic polymer block according to structural formula (IV), (V), or (Va), and (b) a non-zwitterionic block, wherein the non-zwitterionic block includes a polymer selected from the group consisting of poly(lactic-co-glycolic acid), polycaprolactone, polyglycolide, polylactic acid, poly-3-hydroxybutyrate, polydioxanone, polytrimethylenecarbonate, poly(glycolide-co-caprolactone), poly(glycolide-co-trimethylenecarbonate), and poly(dioxanon-co-trimethylenecarbonate-co-glycolide). According to aspects of the present invention, the hydrophobic block has a number average molecular weight from about 1,000 to about 200,000. An assembly composition including a plurality of the diblock copolymers is provided by the present invention. The assembly composition can be in the form of a micelle, a particle, or a polymersome. According to aspects of the present invention, the assembly composition, such as a micelle, a particle, or a polymersome, further includes a therapeutic and/or diagnostic agent. Optionally, the assembly composition includes a pharmaceutically acceptable carrier or diluent.

Diblock copolymers are provided according to aspects of the present invention which include: (a) a carnitine-derived zwitterionic polymer block according to structural formula (IV), (V), or (Va), and (b) a non-zwitterionic block, wherein the non-zwitterionic block comprises a polymer selected from poly(lactic-co-glycolic acid) (PLGA), poly-(Hydroxyethyl)methacrylate (HEMA), poly-acrylamide (PAA), polyethylene glycol (PEG), alginate, polycaprolactone (PCL), polyglycolide (PG), polylactic acid (PLA), poly-3-hydroxybutyrate, polydioxanone, polytrimethylenecarbonate, poly (glycolide-co-caprolactone) (Monocryl™), poly(glycolide-co-trimethylenecarbonate) (Maxon™), and poly(dioxanon-co-trimethylenecarbonate-co-glycolide) (BioSyn™).

According to aspects of the present invention, the hydrophobic block has a number average molecular weight from about 1,000 to about 200,000. An assembly composition including a plurality of the diblock copolymers is provided by the present invention. The assembly composition can be in the form of a micelle, a particle, or a polymersome. According to aspects of the present invention, the assembly composition, such as a micelle, a particle, or a polymersome, further includes a therapeutic and/or diagnostic agent. Optionally, the assembly composition includes a pharmaceutically acceptable carrier or diluent.

According to aspects of the present invention, carnitine-derived zwitterionic polymers having the structural formula (IV):

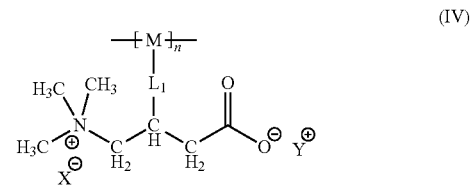

(IV)

are provided, where M is a monomeric repeating unit, $L_1$ is a linker, n is an integer from 1 to about 10000, $X^-$ is a counter ion associated with the cationic center, and $Y^+$ is a counter ion associated with the anionic center, with the proviso that the polymer does not have or include the structure of formula XXX:

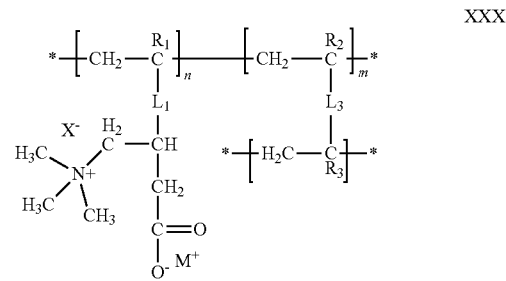

XXX where $R_1$, $R_2$, and $R_3$ are each independently selected from hydrogen, alkyl, and aryl groups; $L_1$ is a linker that covalently couples the polymer sidechain to the polymer backbone; X– is a counter ion associated with the cationic center; $M^+$ is a metal ion, an ammonium ion, or an organic ion; $L_3$ is a linker that covalently couples two polymer backbones; n is an integer in the range of 2 to about 100,000; m is a positive non-zero integer; and m/n is in the range of 0.1%-99.9%.

According to aspects of the present invention, carnitine-derived zwitterionic polymers having the structural formula (IV) are provided, where M is a monomeric repeating unit, $L_1$ is a linker, n is an integer from 1 to about 10000, $X^-$ is a counter ion associated with the cationic center, and $Y^+$ is a counter ion associated with the anionic center, with the proviso that the polymer does not have or include the structure of formula XXX where $R_1$, $R_2$, and $R_3$ are each independently selected from the group consisting of hydrogen, fluorine, trifluoromethyl, $C_1$-$C_6$ alkyl, and $C_6$-$C_{12}$ aryl groups; $L_1$ is —C(=O)O—$(CH_2)_z$— or —C(=O)NH—$(CH_2)_z$—; and z is an integer from 1 to 20.

Methods of synthesizing a carnitine-derived zwitterionic monomer having the structural formula (I) including: combining carnitine or a carnitine salt, hydroquinone and anhydrous dimethylformamide in a reaction vessel purged with nitrogen producing a mixture; heating the mixture to a temperature in the range of 40° C. to 60° C., for a time in the range of 5 minutes to 1 hour, producing a first heated mixture; adding acryloyl chloride to the first heated mixture; heating the first heated mixture to a temperature in the range of 70° C. to 90° C., producing a second heated mixture; absorbing excess HCl from the second heated mixture while reacting the second heated mixture at a temperature in the range of 70° C. to 90° C., for a reaction time in the range of 1 to 5 hours, producing a carnitine-derived zwitterionic monomer having the structural formula (I). According to aspects of the present invention, the carnitine or carnitine salt has a concentration in the range of about 0.01-2 mol/L in dimethylformamide. According to aspects of the present invention, the molar ratio of the carnitine or carnitine salt to acryloyl chloride is in the range from about 20:1 to 1:20. According to aspects of the present invention, the molar ratio of hydroquinone to acryloyl chloride is in the range of about 1:1 to 1:2000. Optionally, the method further includes purification of the carnitine-derived zwitterionic monomer.

Methods of synthesizing a carnitine-derived zwitterionic monomer having the structural formula (I) including: combining L-carnitine or an L-carnitine salt, hydroquinone and anhydrous dimethylformamide in a reaction vessel purged with nitrogen producing a mixture; heating the mixture to a temperature in the range of 40° C. to 60° C., for a time in the range of 5 minutes to 1 hour, producing a first heated mixture; adding acryloyl chloride to the first heated mixture; heating the first heated mixture to a temperature in the range of 70° C. to 90° C., producing a second heated mixture; absorbing excess HCl from the second heated mixture while reacting the second heated mixture at a temperature in the range of 70° C. to 90° C., for a reaction time in the range of 1 to 5 hours, producing an L-carnitine-derived zwitterionic monomer having the structural formula (I). According to aspects of the present invention, the L-carnitine or L-carnitine salt has a concentration in the range of about 0.01-2 mol/L in dimethylformamide. According to aspects of the present invention, the molar ratio of the L-carnitine or L-carnitine salt to acryloyl chloride is in the range from about 20:1 to 1:20. According to aspects of the present invention, the molar ratio of hydroquinone to acryloyl chloride is in the range of about 1:1 to 1:2000. Optionally, the method further includes purification of the L-carnitine-derived zwitterionic monomer.

DETAILED DESCRIPTION OF THE INVENTION

Figure 1:
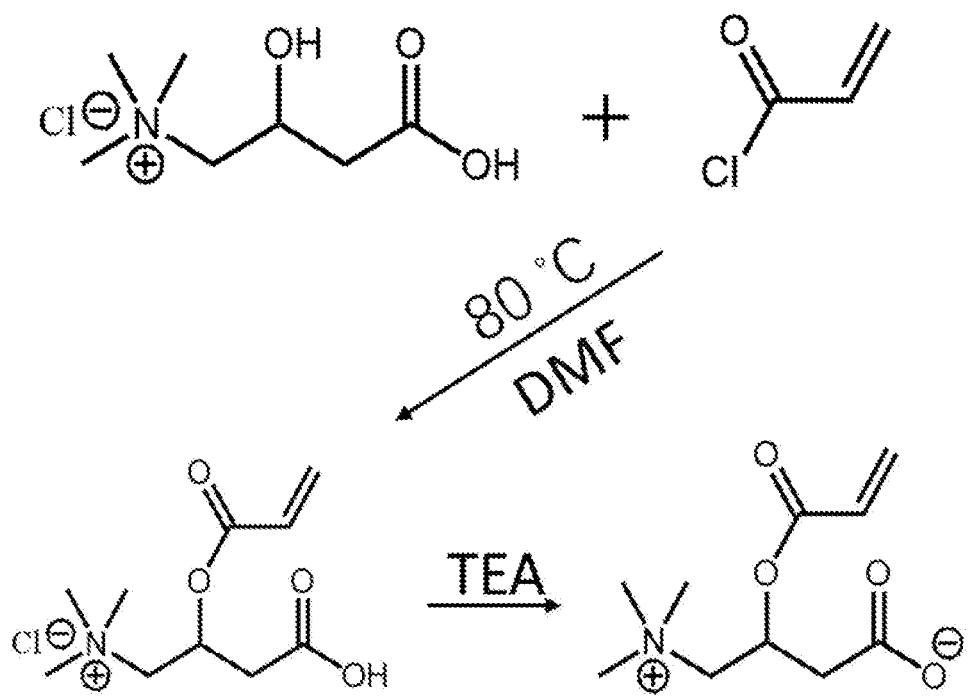
FIG. 1 is a diagram showing a synthetic scheme for an L-carnitine derived zwitterionic acrylate monomer called L-carnitineMA monomer herein.

Carnitine derived zwitterionic materials, methods of synthesizing carnitine derived zwitterionic materials and methods of using carnitine derived zwitterionic materials are provided according to aspects of the present invention.

Carnitine ester materials, methods of synthesizing carnitine ester materials, and methods of using carnitine ester materials, are provided according to aspects of the present invention.

General and specific chemical structures of carnitine derived zwitterionic materials and carnitine ester materials are shown herein below. Several variables associated with the structures shown, including M, $L_1$, Z, $Z_1$, X−, Y+ and $R_1$ are described here and these definitions apply in each structure where the variable is present.

The monomeric repeating unit, M, is not particularly limiting and can be, for example, suitable monomeric repeating units include repeating units for polyesters, polyamides, poly(amino acids), polyimides, polycarbonates, polysiloxanes, polyurethanes, polyphosphazenes, acrylic polymers, amino resins, epoxy resins, phenolic resins, and alkyd resins.

$L_1$ is a linker that covalently couples the carnitine molecule to the monomeric repeating unit. Representative $L_1$ groups include —C(=O)O—$(CH_2)_{n1}$— and —C(=O)NH—$(CH_2)_{n1}$—, where n1 is an integer from 1 to 20 (e.g., 3).

X− is a counter ion associated with the cationic center. The counter ion X− can be the counter ion that results from the synthesis of the cationic polymers or the monomers (e.g., halides such as Cl−, Br−, and I−). The counter ion X− that is initially produced from the synthesis of the cationic center can also be exchanged with other suitable counter ions to provide polymers having controllable hydrolysis properties and other biological properties. Representative hydrophobic counter ions X− include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions X− also can be chosen from halides such as chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof. Other suitable counter ions X− include hydrophobic counter ions and counter ions having therapeutic activity (e.g., an antimicrobial agent, such as salicylic acid (2-hydroxybenzoic acid), benzoate, and lactate.

$Y^+$ is a counter ion associated with the anionic center. At each occurrence $Y^+$ is a metal ion (e.g., sodium, lithium, potassium, calcium), ammonium ion (e.g., $NR_4^+$, where each R is the same or different and selected from hydrogen, alkyl, and aryl), or an organic ion.

Z is an alkyl, aryl, acyl, or silyl group, where the alkyl, aryl, acyl, or silyl group is optionally further substituted with one or more substituents. According to particular aspects Z is selected from $C_1$-$C_{20}$ alkyl, $C_6$-$C_{12}$ aryl, cyclic alkyl (e.g., isobornyl, cyclohexyl, cyclopentyl), and fluoroalkyl (e.g., perfluorobutyl, perfluoroethyl).

By way of non-limiting example, $Z_1$ can be selected from, but not limited to, tert-butyl (Bu), 2-chlorotrityl (2-Cl-Trt), 2,4-dimethoxybenzyl (Dmb), 2-phenylisopropyl (2-PhiPr), 5-phenyl-3,4-ethylenedioxythenyl (phenyl-EDOTn), and a derivative of any thereof; or a benzyl group and a derivative thereof.

$R_1$ is selected from the group consisting of: hydrogen, fluorine, trifluoromethyl, $C_1$-$C_6$ alkyl, and $C_6$-$C_{12}$ aryl.

Carnitine Derived Zwitterionic Materials

Carnitine derived zwitterionic materials provided according to aspects of the present invention include carnitine derived zwitterionic monomers, their polymers, copolymers, lipid-polymer conjugates, protein-polymer conjugates, and hydrogels.

Carnitine Derived Zwitterionic Monomers

A general structural formula for a carnitine-derived material which is a monomer is shown herein as structure (I):

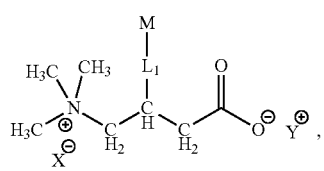

(I)

where M is a monomeric repeating unit, $L_1$ is a linker, X– is a counter ion associated with the cationic center of structure (I) and Y+ is a counter ion associated with the anionic center of structure (I).

A specific structural formula for a carnitine-derived material which is a monomer is shown herein as structure (II)

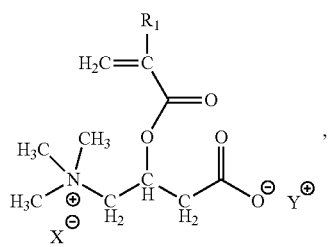

(II)

where $R_1$ is selected from the group consisting of: hydrogen, fluorine, trifluoromethyl, $C_1$-$C_6$ alkyl, and $C_6$-$C_{12}$ aryl groups, X– is a counter ion associated with the cationic center of structure (II) and Y+ is a counter ion associated with the anion center of structure (II).

A specific structural formula for a carnitine-derived material which is L-carnitine derived zwitterionic acrylate monomer is shown herein as structure (IIa)

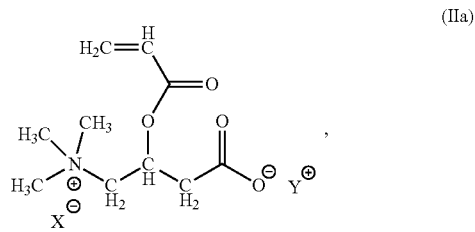

(IIa)

where X– is a counter ion associated with the cationic center of structure (IIa) and Y+ is a counter ion associated with the anion center of structure (IIa).

A specific structural formula for a carnitine-derived material which is a monomer is shown herein as structure (III)

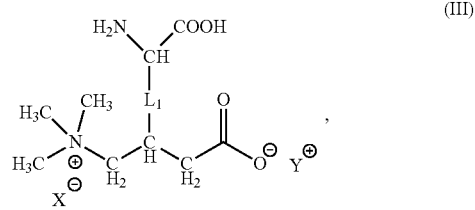

(III)

where $L_1$ is a linker that covalently couples the carnitine molecule to the amino acid unit, X– is a counter ion associated with the cationic center of structure (III) and Y+ is a counter ion associated with the anion center of structure (III).

A carnitine derived zwitterionic monomer according to aspects of the present invention can be a D-carnitine derived zwitterionic monomer or an L-carnitine derived zwitterionic monomer. Compositions according to aspects of the present invention include a D-carnitine derived zwitterionic monomer, an L-carnitine derived zwitterionic monomer or a mixture of both a D-carnitine derived zwitterionic monomer and an L-carnitine derived zwitterionic monomer.

An L-carnitine derived zwitterionic acrylate monomer (L-carnitineMA) is provided according to aspects of the present invention, shown in FIG. 1.

Carnitine Derived Zwitterionic Polymers

A general structural formula for a carnitine-derived material which is a polymer is shown herein as structure (IV):

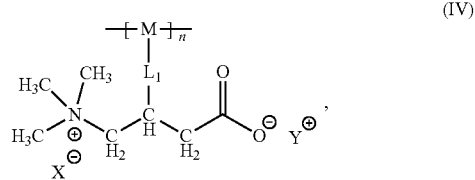

(IV)

where M is a monomeric repeating unit, $L_1$ is a linker, n is an integer from 1 to about 10000, $X^-$ is a counter ion associated with the cationic center, and $Y^+$ is a counter ion associated with the anionic center.

A specific structural formula for a carnitine-derived material which is a polymer is shown herein as structure (V):

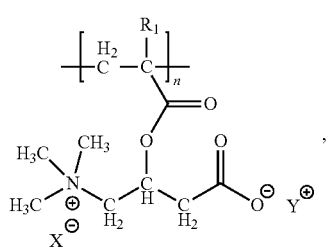

where $R_1$ is selected from the group consisting of hydrogen, fluorine, trifluoromethyl, $C_1$-$C_6$ alkyl, and $C_6$-$C_{12}$ aryl groups, n is an integer from 1 to about 10000, $X^-$ is a counter ion associated with the cationic center, and $Y^+$ is a counter ion associated with the anionic center.

A specific structural formula for a carnitine-derived material which is a polymer of L-carnitine derived zwitterionic acrylate monomer is shown herein as structure (Va):

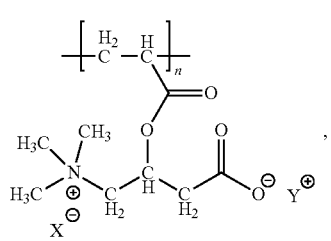

where n is an integer from 1 to about 10000, $X^-$ is a counter ion associated with the cationic center, and $Y^+$ is a counter ion associated with the anionic center.

A specific structural formula for a carnitine-derived material which is a polymer is shown herein as structure (VI):

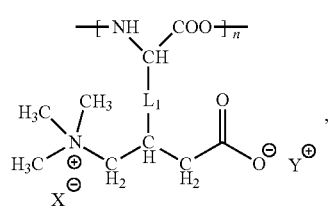

where $L_1$ is a linker that covalently couples the carnitine molecule to the amino acid repeating units as shown and n is an integer from 1 to about 10000. Representative $L_1$ groups include —C(═O)O—(CH$_2$)$_{n1}$— and —C(═O)NH—(CH$_2$)$_{n1}$—, where n1 is an integer from 1 to 20 (e.g., 3).

Methods of Synthesis of Carnitine Derived Zwitterionic Materials

Provided according to aspects of the present invention is a single-step synthesis protocol to obtain a novel zwitterionic carboxybetaine monomer using carnitine as a natural product starting material, i.e. carnitine derived zwitterionic materials.

A method of synthesizing a carnitine-derived zwitterionic monomer having the structural formula (I) includes combining carnitine, hydroquinone and anhydrous dimethylformamide according to aspects of the present invention. In one example, L-carnitine is used and the method includes: combining L-carnitine hydrochloride, hydroquinone and anhydrous dimethylformamide in a container purged with nitrogen to produce a mixture; heating the mixture to a temperature in the range of 40° C. to 60° C., such as 40° C., for a time in the range of 5 minutes to 1 hour, such as 10 minutes, to produce a first heated mixture; adding acryloyl chloride to the first heated mixture; heating the first heated mixture to a temperature in the range of 70° C. to 90° C., such as 80° C., to produce a second heated mixture; absorbing excess HCl from the second heated mixture while reacting the second heated mixture at a temperature in the range of 70° C. to 90° C., such as 80° C. for a reaction time in the range of 1 to 5 hours, such as 3 hours, producing a carnitine-derived zwitterionic monomer having the structural formula (I).

According to aspects of the present invention, the carnitine or carnitine salt monomer has a concentration in the range of about 0.01-2 mol/L in dimethylformamide. The molar ratio of the carnitine or carnitine salt to acryloyl chloride is in the range from about 20:1 to 1:20. The molar ratio of hydroquinone to acryloyl chloride is in the range of about 1:1 to 1:2000.

According to aspects of the present invention, the carnitine or carnitine salt monomer has a concentration in the range of about 0.1-1 mol/L in dimethylformamide. The molar ratio of the carnitine or carnitine salt to acryloyl chloride is in the range from about 1:1 to 1:10. The molar ratio of hydroquinone to acryloyl chloride is in the range of about 1:500 to 1:1500.

According to aspects of the present invention, L-carnitine hydrochloride is the carnitine salt used and the L-carnitine hydrochloride has a concentration of 0.2-0.5 mol/L in dimethylformamide. The molar ratio of L-carnitine hydrochloride to acryloyl chloride ranges from 1:2 to 1:6. The molar ratio of hydroquinone/acryloyl chloride is 1:1000.

A method of synthesis of a purified carnitine-derived zwitterionic monomer having the structural formula (I) optionally includes purification of the carnitine-derived zwitterionic monomer.

Optionally, the purification includes removal of excess acryloyl chloride to produce a purified carnitine-derived zwitterionic monomer having the structural formula (I).

In a further option, the purification includes precipitation of unreacted L-carnitine hydrochloride to produce precipitated L-carnitine hydrochloride and removal of the precipitated L-carnitine hydrochloride to produce a purified carnitine-derived zwitterionic monomer having the structural formula (I).

In a further option, purification includes precipitating the carnitine-derived zwitterionic monomer having the structural formula (I).

In a still further option, purification includes dissolving the precipitate in anhydrous methanol stirred with activated charcoal at a temperature in the range of 30° C. to 50° C., such as 40° C., for a time in the range of 30 minutes to 5 hours, such as 2 hours, to produce an activated charcoal mixture; centrifuging the activated charcoal mixture to produce a pellet and supernatant; adding diethyl ether to the supernatant, producing a supernatant mixture and drying the supernatant mixture under vacuum to produce a purified carnitine-derived zwitterionic monomer having the structural formula (I) in powder form.

A zwitterionic monomer (L-carnitineMA) according to aspects of the present invention was prepared by a single-step reaction according to further aspects of the present invention including reacting L-carnitine with acryloyl chloride as shown in FIG. 1 and described in Example 1.

Polymer coatings according to aspects of the present invention were prepared by atom-transfer radical-polymerization (ATRP) and hydrogels through crosslinking, and the anti-fouling performance was verified using surface plasmon resonance (SPR) sensor and enzyme-linked immunosorbent assay (ELISA) test to quantify protein adsorption, and assays to evaluate bacterial adhesion.

Carnitine derived zwitterionic materials provided by the present invention are useful in various ways such as, but not limited to, polymer surface coatings with superior antifouling performance, bulk hydrogel materials with superior antifouling performance; cell encapsulation materials; tissue engineering materials; and drug delivery carriers.

Carnitine derived zwitterionic material: polymer modified therapeutic and diagnostic agents A conjugate is provided according to aspects of the present invention, wherein a carnitine-derived zwitterionic polymer is covalently coupled to a therapeutic and/or diagnostic agent, wherein the carnitine-derived zwitterionic polymer has the structural formula (IV).

A conjugate is provided according to aspects of the present invention, wherein a carnitine-derived zwitterionic polymer is covalently coupled to a therapeutic and/or diagnostic agent, wherein the carnitine-derived zwitterionic polymer has the structural formula shown below, wherein R2, R3, R4, R5, and R6 is each independently selected from a reactive functional group such as but not limited to, amine group, hydroxyl group, aldehyde group, carboxylic acid group, etc., wherein each of M, M1, and M2 is independently a monomeric repeating unit, $L_1$, $L_2$ is each independently a linker, n, n1, n2 is each independently an integer from 1 to about 10000, $X^-$ is a counter ion associated with the cationic center, and $Y^+$ is a counter ion associated with the anionic center.

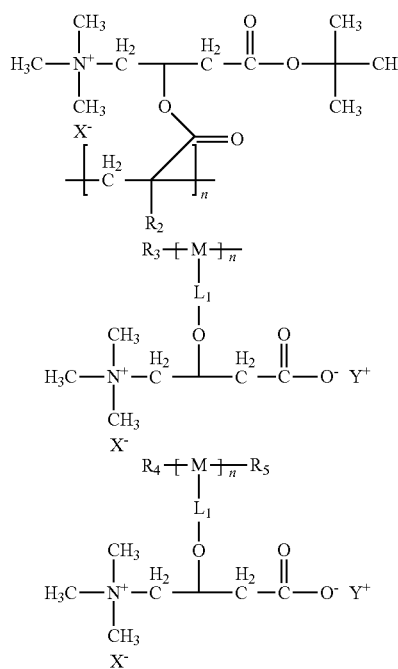

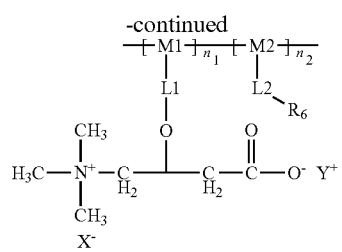

According to aspects of the present invention, a conjugate including a carnitine-derived zwitterionic polymer covalently coupled to a therapeutic and/or diagnostic agent, wherein the carnitine-derived zwitterionic polymer has the structural formula (IV), is produced by reaction of a carnitine-derived polymer having a reactive functional terminal group with a therapeutic and/or diagnostic agent, generating the conjugate, as further described herein.

A specific structural formula for a carnitine-derived polymer having a reactive functional terminal group is shown herein as structure (XXV):

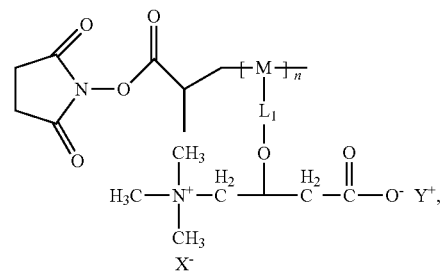

(XXV)

where M is a monomeric repeating unit, $L_1$ is a linker, n is an integer from 1 to about 10000, $X^-$ is a counter ion associated with the cationic center, and $Y^+$ is a counter ion associated with the anionic center.

A specific structural formula for a carnitine-derived polymer having a reactive functional terminal group is shown herein as structure (XXVII):

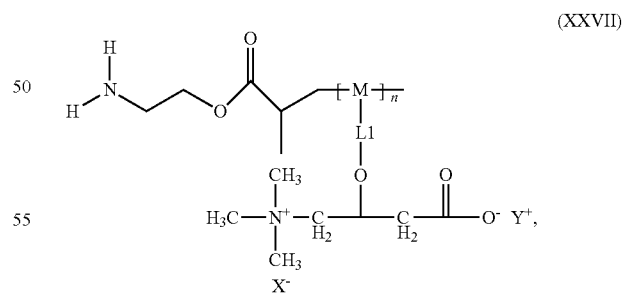

(XXVII)

where M is a monomeric repeating unit, $L_1$ is a linker, n is an integer from 1 to about 10000, $X^-$ is a counter ion associated with the cationic center, and $Y^+$ is a counter ion associated with the anionic center.

In certain embodiments, the therapeutic agent or diagnostic agent in the conjugate is selected from small molecules, organometallic compounds, nucleic acids, proteins (including multimeric proteins, protein complexes, peptides), lipids, carbohydrates, hormones, metals, radioactive elements and compounds, drugs, vaccines, immunological agents, and/or combinations thereof.

In some embodiments, the therapeutic agent is a small molecule and/or organic compound with pharmaceutical activity. In some embodiments, the therapeutic agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, anti-mitotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitor of DNA, RNA, or protein synthesis and/or a combination of any two or more thereof.

In certain embodiments, a small molecule therapeutic agent can be any drug. In some embodiments, the drug is one that has already been deemed safe and effective for use in humans or animals by the appropriate governmental agency or regulatory body. For example, drugs approved for human use are listed by the FDA under 21 C.F.R.§§ 330.5, 331 through 361, and 440 through 460, incorporated herein by reference; drugs for veterinary use are listed by the FDA under 21 C.F.R.§§ 500 through 589, incorporated herein by reference. All listed drugs are considered acceptable for use in accordance with the present invention.

A more complete listing of classes and specific drugs suitable for use in the present invention may be found in Pharmaceutical Drugs: Syntheses, Patents, Applications by Axel Kleemann and Jurgen Engel, Thieme Medical Publishing, 1999 and the Merck Index: An Encyclopedia of Chemicals, Drugs and Biologicals, Ed. by Budavari et al, CRC Press, 1996, both of which are incorporated herein by reference.

In certain embodiments of the invention, the therapeutic agent is a nucleic acid (e.g., DNA, RNA, derivatives thereof). In some embodiments, the nucleic acid agent is a functional RNA. In general, a "functional RNA" is an RNA that does not code for a protein but instead belongs to a class of RNA molecules whose members characteristically possess one or more different functions or activities within a cell. It will be appreciated that the relative activities of functional RNA molecules having different sequences may differ and may depend at least in part on the particular cell type in which the RNA is present. Thus the term "functional RNA" is used herein to refer to a class of RNA molecule and is not intended to imply that all members of the class will in fact display the activity characteristic of that class under any particular set of conditions. In some embodiments, functional RNAs include RNAi-inducing entities (e.g., short interfering RNAs (siRNAs), short hairpin RNAs (shRNAs), and microRNAs), ribozymes, tRNAs, rRNAs, RNAs useful for triple helix formation.

In some embodiments, the nucleic acid agent is a vector. As used herein, the term "vector" refers to a nucleic acid molecule (typically, but not necessarily, a DNA molecule) which can transport another nucleic acid to which it has been linked. A vector can achieve extra-chromosomal replication and/or expression of nucleic acids to which they are linked in a host cell. In some embodiments, a vector can achieve integration into the genome of the host cell.

In some embodiments, vectors are used to direct protein and/or RNA expression. In some embodiments, the protein and/or RNA to be expressed is not normally expressed by the cell. In some embodiments, the protein and/or RNA to be expressed is normally expressed by the cell, but at lower levels than it is expressed when the vector has not been delivered to the cell. In some embodiments, a vector directs expression of any of the functional RNAs described herein, such as RNAi-inducing entities, ribozymes.

In some embodiments, the therapeutic agent may be a protein or peptide. The terms "protein," "polypeptide," and "peptide" can be used interchangeably. In certain embodiments, peptides range from about 5 to about 5000, 5 to about 1000, about 5 to about 750, about 5 to about 500, about 5 to about 250, about 5 to about 100, about 5 to about 75, about 5 to about 50, about 5 to about 40, about 5 to about 30, about 5 to 30 about 25, about 5 to about 20, about 5 to about 15, or about 5 to about 10 amino acids in size.

Polypeptides may contain L-amino acids, D-amino acids, or both and may contain any of a variety of amino acid modifications or analogs known in the art. Useful modifications include, e.g., terminal acetylation, amidation. In some embodiments, polypeptides comprise natural amino acids, unnatural amino acids, synthetic amino acids, and combinations thereof, as described herein.

In some embodiments, the therapeutic agent is a hormone, erythropoietin, insulin, cytokine, antigen for vaccination, growth factor. In some embodiments, the therapeutic agent may be an antibody and/or characteristic portion thereof. In some embodiments, antibodies include, but are not limited to, polyclonal, monoclonal, chimeric (i.e., "humanized"), or single chain (recombinant) antibodies. In some embodiments, antibodies have reduced effector functions and/or bispecific molecules. In some embodiments, antibodies include Fab fragments and/or fragments produced by a Fab expression library (e.g. Fab, Fab', F(ab')2, scFv, Fv, dsFv diabody, and Fd fragments).

In some embodiments, the therapeutic agent is a carbohydrate. In certain embodiments, the carbohydrate is a carbohydrate that is associated with a protein (e.g. glycoprotein, proteoglycan). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

In some embodiments, the therapeutic agent is a lipid. In certain embodiments, the lipid is a lipid that is associated with a protein (e.g., lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g., vitamin E), phospholipids, sphingolipids, and lipoproteins.

In some embodiments, the lipid includes one or more fatty acid groups or salts thereof. In some embodiments, the fatty acid group includes digestible, long chain (e.g., C8-C50), substituted or unsubstituted hydrocarbons. In some embodiments, the fatty acid group is one or more of butyric, caproic, caprylic, capric, lauric, myristic, palmitic, stearic, arachidic, behenic, or lignoceric acid. In some embodiments, the fatty acid group is one or more of palmitoleic, oleic, vaccenic, linoleic, alpha-linolenic, gamma-linoleic, arachidonic, gadoleic, arachidonic, eicosapentaenoic, docosahexaenoic, or erucic acid.

Diagnostic Agents

In certain embodiments, a conjugate according to the present invention includes one or more diagnostic agents. In some embodiments, an included diagnostic agent includes a commercially available imaging agent used in positron emissions tomography (PET), computer assisted tomography (CAT), single photon emission computerized tomography, x-ray, fluoroscopy, and magnetic resonance imaging (MRI); anti-emetics; and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, a diagnostic and/or therapeutic agent included in a conjugate composition or the present invention is a radionuclide. Among the radionuclides used, gamma-emitters, positron-emitters, and X-ray emitters are suitable for diagnostic and/or therapeutic purposes, while beta emitters and alpha-emitters may also be used for therapy. Suitable radionuclides for use in the invention include, but are not limited to, 123I, 125I, 130I, 131I, 133I, 135I, 47Sc, 72As, 72Se, 90Y, 88Y, 97Ru, 100Pd, 101mRh, 119Sb, 128Ba, 197Hg, 211At, 212Bi, 212Pb, 109Pd, 111In, 67Ga, 68Ga, 67Cu, 75Br, 77Br, 99mTc, 14C, 13N, 15O, 32P, 33P, and 18F.

In some embodiments, a diagnostic agent included in a conjugate composition of the present invention is a fluorescent, luminescent, or magnetic moiety. Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes. Fluorescent and luminescent moieties include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein. Luminescent proteins include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9th edition, 2002; and The Handbook-A Guide to Fluorescent Probes and Labeling Technologies, Invitrogen, 10th edition, available at the Invitrogen web site).

In some embodiments, a diagnostic agent included in a conjugate composition of the present invention is nanoparticles which can be detected by certain diagnostic methods, such as quantum dots, iron oxide, gold nanoparticles, nano-rod or nano-shell, carbon nanotube, nano-sheet, silica protected nanoparticles or combinations of these nano-materials.

In certain embodiments, such nanoparticles further include one or more therapeutic agents and/or one or more diagnostic agents.

In certain embodiments, reaction of a carnitine-derived polymer having a reactive functional terminal group with a therapeutic and/or diagnostic agent, generates a conjugate wherein the linkage between the polymer and the therapeutic or diagnostic agent is degradable.

In certain embodiments, the linkage between the carnitine-derived polymer and the therapeutic or diagnostic agent is degradable under certain conditions, allowing the release of the agents at certain environment (e.g., the disease site).

In certain embodiments, the linkage between the carnitine-derived polymer and the therapeutic or diagnostic agent is hydrolysable including but not limited to a carboxylate ester, a phosphate ester, a carbamate, an anhydride, an acetal, a ketal, an acyloxyalkyl ether, an imine, a hydrazone, an orthoester, a thioester, a carbonate, a peptide, an oligonucleotide, etc.

In certain embodiments, the linkage between the carnitine-derived polymer and the therapeutic or diagnostic agent is enzymatically degradable including but not limited to a tobacco etch virus protease (TEV) cleavable sequence, a trypsin cleavable sequence, a thrombin cleavable sequence, a cathepsin B cleavable sequence, a cathespin D cleavable sequence, a cathepsin K cleavable sequence, a caspase cleavable sequence, a matrix metalloproteinase, a phosphodiester, a phospholipid, an ester, a beta-glactose, etc., where the linkage is degraded by one or more enzymes.

In certain embodiments, the linkage between the carnitine-derived polymer and the therapeutic or diagnostic agent is cleavable under nucleophilic or basic condition, including but not limited to a dialkyl dialkoxysilane, a cyanoethyl group, a sulfone, an ethyleneglycolyl disuccinate, a 2-N-acyl nitrobenzenesulfonamide, an alpha-thiophenylester, an unsaturated vinyl sulfide, a sulfonamide after activation, a malondialdehyde (MDA)-indole derivative, a levulinoyl ester, a hydrazone, an acylhydrazone, an alkyl thioester, etc.

In certain embodiments, the linkage between the carnitine-derived polymer and the therapeutic or diagnostic agent is cleavable under reducing agents or environment, including but not limited to a disulfide, an azo compound, etc.

In certain embodiments, the linkage between the carnitine-derived polymer and the therapeutic or diagnostic agent is cleavable under photo irradiation, including but not limited to a 2-nitrobenzyl derivative, a phenacyl ester, a 8-quinolinyl benzenesulfonate, a coumarin, a phosphotriester, a bis-arylhydrazone, a bimane bi-thiopropionic acid derivative, etc.

In certain embodiments, the linkage between the carnitine-derived polymer and the therapeutic or diagnostic agent is cleavable under electrophilic or acidic condition, including but not limited to a paramethoxybenzyl derivative, a tert-butylcarbamate analogue, a dialkyl or diaryl dialkoxysilane, an orthoester, an acetal, an aconityl, a hydrazone, a beta-thiopropionate, a phosphoramidate, an imine, a trityl, a vinyl ether, a polyketal, an alkyl 2-(diphenylphosphino) benzoate derivative, etc.

In certain embodiments, the linkage between the carnitine-derived polymer and the therapeutic or diagnostic agent is cleavable under oxidizing condition, including but not limited to a vicinal diol, a selenium compound, etc.

Methods of Synthesis of Therapeutic Agent or Diagnostic Agent-Carnitine-Derived Polymer Conjugate A method of synthesizing a carnitine-derived zwitterionic polymer-therapeutic or diagnostic agent conjugate includes, but is not limited to, covalently coupling a suitably functionalized carnitine-derived zwitterionic polymer (e.g., having an end terminal amino, carboxylic acid, NHS ester group, or other functional group) or their hydrophobic derivatives (e.g., carnitine ester materials) to a therapeutic or diagnostic agent with suitable functional groups (e.g., having an carboxylic acid, amino, thiol group, or reactive derivative thereof).

A further method of synthesizing a carnitine-derived zwitterionic polymer-therapeutic or diagnostic agent conjugate includes preparing a radical initiator based on the therapeutic or diagnostic agent (e.g., the agent functionalized to include a terminal radical initiator group) followed by polymerization of a suitable carnitine-derived monomer of the present invention, or a hydrophobic derivatives thereof (e.g., a carnitine ester monomer).

provided by the present invention are useful in various ways such as, but not limited to, forming an assembly, comprising a plurality of the conjugates in the form of, but not limited to, a micelle or a particle, and forming a composition, comprising the assembly and a pharmaceutically accepted carrier or diluent. They are useful for therapeutic and diagnostic purposes.

Carnitine derived zwitterionic material: Lipid-polymer conjugate

A conjugate is provided according to the present invention including a carnitine-derived zwitterionic polymer covalently coupled to a lipid, wherein the carnitine-derived zwitterionic polymer has the structural formula (IV).

A specific structural formula for a carnitine-derived zwitterionic polymer covalently coupled to a lipid, wherein the carnitine-derived zwitterionic polymer has the structural formula (IV) and wherein the lipid is distearoylphosphatidylethanolamine (DSPE), shown herein as structure (XXVI):

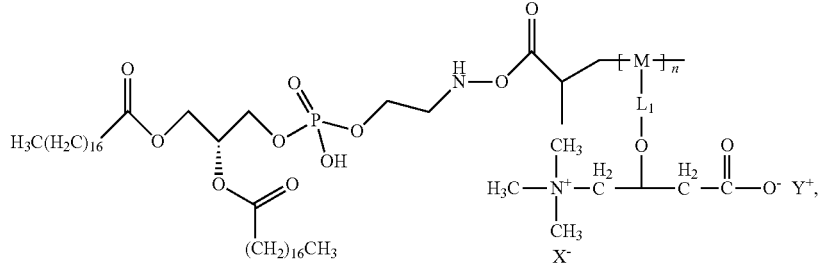

A further method of synthesizing a carnitine-derived zwitterionic polymer-therapeutic or diagnostic agent conjugate includes preparing a monomer based on the therapeutic or diagnostic agent (e.g., the agent functionalized to include polymerizable monomer group) followed by co-polymerization with a suitable carnitine-derived monomer, or their hydrophobic derivatives (e.g., carnitine ester monomer). In the case when a carnitine hydrophobic derivative(s) (e.g., carnitine ester monomer or polymer) is involved, a de-protection procedure is performed after the carnitine hydrophobic derivative(s) and the therapeutic or diagnostic agent(s) is covalently linked to generate a zwitterionic carnitine-derived structure in the conjugate.

Reactive group terminated zwitterionic carnitine-derived polymers, such as an NHS ester terminated zwitterionic carnitine-derived polymer and an amino group terminated zwitterionic carnitine-derived polymer according to aspects of the present invention can be prepared as described in Example 2.

An insulin-zwitterionic carnitine-derived polymer conjugate according to aspects of the present invention was prepared by a covalently coupling reaction according to further aspects of the present invention including reacting NHS ester terminated carnitine derived zwitterionic polymer with amino groups on insulin.

A paclitaxel (TXL) zwitterionic carnitine-derived polymer conjugate according to aspects of the present invention was prepared by a copolymerization of TXL derived monomer and carnitine t-Bu ester monomer, followed by deprotection of t-Bu groups.

Conjugates including a carnitine derived zwitterionic polymer and a therapeutic agent and/or diagnostic agent where M is a monomeric repeating unit, $L_1$ is a linker, n is an integer from 1 to about 10000, $X^-$ is a counter ion associated with the cationic center, and $Y^+$ is a counter ion associated with the anionic center.

In certain embodiments, the lipid in a carnitine-derived zwitterionic polymer covalently coupled to a lipid, wherein the carnitine-derived zwitterionic polymer has the structural formula (IV) is selected from synthetic lipids and naturally-occurring lipids.

In certain embodiments, the lipid in a carnitine-derived zwitterionic polymer covalently coupled to a lipid, wherein the carnitine-derived zwitterionic polymer has the structural formula (IV) is a phospholipid, a sphingolipid, or a sterol.

In certain embodiments, the lipid in a carnitine-derived zwitterionic polymer covalently coupled to a lipid, wherein the carnitine-derived zwitterionic polymer has the structural formula (IV) contains a reactive functional group, such as an amine group, hydroxyl group, aldehyde group, or carboxylic acid group, at its polar head group, wherein the reactive functional group is suitable for reaction with a reactive group terminated zwitterionic carnitine-derived polymer resulting a conjugate wherein a carnitine-derived zwitterionic polymer is covalently coupled to a lipid.

In certain embodiments, the lipid in the lipid-polymer conjugate includes two hydrocarbon chains, such as phosphatidylethanolamine (PE), phosphatidylglycerol (PG), phosphatidic acid (PA), or phosphatidylinositol (PI), where each hydrocarbon chain contain 3-24 carbon atoms in length and have varying degrees of unsaturation.

In certain embodiments, the lipid in the lipid-polymer conjugate is a diacylphosphatidylethanolamine, a ceramide, a sphingomyelin, a dihydrosphingomyelin, a cephalin, or a cerebroside. For the diacyl compounds, the acyl group is a fatty acid group (e.g., C8-C40).

In certain embodiments, the lipid in the lipid-polymer conjugate is a diacylphosphatidylethanolamine or a diacylphosphatidylglycerol.

In certain embodiments, the lipid in the lipid-polymer conjugate is selected from the group consisting of dioleoylphosphatidylglycerol (DOPG), dipalmitoylphosphatidylglycerol (DPPG), dioleoyl-phosphatidylethanolamine (DOPE), palmitoyloleoyl-phosphatidylethanolamine (POPE), dipalmitoyl phosphatidyl ethanolamine (DPPE), dimyristoylphosphoethanolamine (DMPE), distearoyl-phosphatidylethanolamine (DSPE), 16-O-monomethyl-phosphoethanolamine, 16-O-dimethyl-phosphoethanolamine, 18-1-trans-phosphoethanolamine, 1-stearoyl-2-oleoyl-phosphatidyethanolamine (SOPE), and 1,2-dioleoyl-sn-glycero-3-phophoethanolamine (transDOPE).

Methods of Synthesis of Lipid-Polymer Conjugate

A method of synthesizing a carnitine-derived zwitterionic polymer-lipid conjugate includes covalently coupling a suitably functionalized lipid moiety (e.g., end terminal amino) to a suitably functionalized zwitterionic carnitine-derived polymer (e.g., end terminal carboxy group or reactive derivative thereof) or their hydrophobic derivatives (e.g., carnitine ester materials).

A DSPE-carnitine polymer conjugate according to aspects of the present invention was prepared by a covalently coupling reaction according to further aspects of the present invention including reacting NHS ester terminated carnitine t-Bu ester polymer with DSPE followed by deprotection of t-Bu groups as described in Example 3.

Carnitine derived zwitterionic polymer-lipid conjugates provided by the present invention are useful in various ways such as, but not limited to, forming an assembly, comprising a plurality of the conjugates in the form of but not limited to a micelle, a liposome, or a polymersome, forming a composition, comprising the assembly and a pharmaceutically acceptable carrier or diluent, forming an assembly comprising a therapeutic and/or diagnostic agent.

Carnitine Derived Zwitterionic Material: Diblock Copolymer

In one aspect, the invention provides a carnitine-derived material which is a diblock copolymer. In one embodiment, the diblock copolymer includes: (a) a zwitterionic block according to structural formula (IV), and (b) a non-zwitterionic block.

In one embodiment, the diblock copolymer includes: (a) a zwitterionic block according to structural formula (IV), and (b) a hydrophobic block.

In one embodiment the non-zwitterionic block includes a homopolymer or copolymer In one embodiment the non-zwitterionic block includes a biodegradable polymer.

In one embodiment the non-zwitterionic block includes a polymer selected from poly(lactic-co-glycolic acid) (PLGA), poly-(Hydroxyethyl)methacrylate (HEMA), polyacrylamide (PAA), polyethylene glycol (PEG), alginate, polycaprolactone (PCL), polyglycolide (PG), polylactic acid (PLA), poly-3-hydroxybutyrate, polydioxanone, polytrimethylenecarbonate, poly(glycolide-co-caprolactone) (Monocryl™), poly(glycolide-co-trimethylenecarbonate) (Maxon™), and poly(dioxanon-co-trimethylenecarbonate-co-glycolide) (BioSyn™).

In one embodiment the non-zwitterionic block includes a polymer selected from the group consisting of poly(lactic-co-glycolic acid) (PLGA), polycaprolactone, polyglycolide, polylactic acid, poly-3-hydroxybutyrate, polydioxanone, polytrimethylenecarbonate, poly(glycolide-co-caprolactone), poly(glycolide-co-trimethylenecarbonate), and poly(dioxanon-co-trimethylenecarbonate-co-glycolide).

In certain embodiments, the non-zwitterionic block has a number average molecular weight from about 1,000 to about 200,000.

Methods of Synthesis of Diblock Copolymer

A method of synthesizing a carnitine-derived zwitterionic polymer-containing diblock copolymer includes preparing a radical initiator based on the non-zwitterionic block (e.g., the polymer functionalized to include a terminal radical initiator group) followed by polymerization of a suitable carnitine-derived monomer, or covalently coupling a suitably functionalized non-zwitterionic polymer (e.g., having an end terminal amino group) to a suitably functionalized zwitterionic carnitine-derived polymer (e.g., having an end terminal carboxy group or reactive derivative thereof) or their hydrophobic derivatives (e.g., carnitine ester materials).

A PLGA-carnitine polymer block copolymer according to aspects of the present invention was prepared by a covalently coupling reaction according to further aspects of the present invention including reacting $NH_2$ terminated carnitine t-Bu ester polymer with COOH terminated PLGA followed by deprotection of t-Bu groups as described in Example 4.

Carnitine derived zwitterionic polymer based diblock copolymers provided by the present invention are useful in various ways such as, but not limited to, forming an assembly, comprising a plurality of the conjugates in a form such as, but not limited to, a micelle, a polymersome, or a particle, forming a composition, comprising the assembly and a pharmaceutically accepted carrier or diluent, forming an composition comprising a therapeutic and/or diagnostic agent.

Carnitine Ester Materials

Carnitine esters are provided according to aspects of the present invention. Carnitine ester cationic monomers are provided according to aspects of the present invention. Polymers, copolymers, lipid-polymer conjugates, protein-polymer conjugates, and hydrogels which incorporate the carnitine ester monomers and their reaction products are provided according to aspects of the present invention.

Carnitine Ester Cationic Monomers

A general structural formula for a carnitine ester cationic monomer is shown herein as structure (VII):

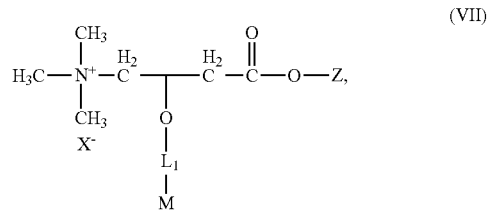

(VII)

where M is a monomeric repeating unit, $L_1$ is a linker, $X^-$ is a counter ion associated with the cationic center, and Z is an alkyl, aryl, acyl, or silyl group, where the alkyl, aryl, acyl, or silyl group is optionally further substituted with one or more substituents.

A general structural formula for a carnitine ester cationic monomer is shown herein as structure (VIII):

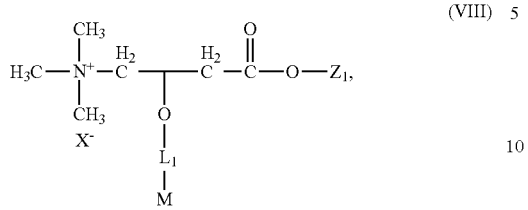

(VIII)

where M is a monomeric repeating unit, $L_1$ is a linker, $X^-$ is a counter ion associated with the cationic center, and $Z_1$ is a protecting group.

The term "protecting group," as used herein, refers to a group that masks or blocks a functional moiety, e.g., O. The presence of the protecting group allows a reaction to be carried out selectively at another reactive site in a carnitine ester cationic material. The protecting group is preferably selectively removable by well-known reagents that do not attack the other functional groups. By way of non-limiting example, As noted above, $Z_1$ can be selected from, but not limited to, tert-butyl (Bu), 2-chlorotrityl (2-Cl-Trt), 2,4-dimethoxybenzyl (Dmb), 2-phenylisopropyl (2-PhiPr), 5-phenyl-3,4-ethylenedioxythenyl (phenyl-EDOTn), and a derivative of any thereof; or a benzyl group and a derivative thereof. These and other suitable protecting groups are described in Greene's Protecting Groups in Organic Synthesis, P. G. M. Wuts, 5th ed., Wiley, 2014, the entirety of which is incorporated herein by reference.

As an example, a typical condition for removal of tert-butyl (Bu), 2-chlorotrityl (2-Cl-Trt), 2,4-dimethoxybenzyl (Dmb), 2-phenylisopropyl (2-PhiPr), 5-phenyl-3,4-ethylenedioxythenyl (phenyl-EDOTn), or a derivative of any thereof, is to treat a compound containing the protecting group with trifluoroacetic acid containing solvents.

As an example, a typical condition for removal of benzyl groups, or a derivative of any thereof, is to treat a compound containing the protecting group with $NaBH_4$ containing solvents.

A general structural formula for a carnitine ester cationic monomer is shown herein as structure (IX):

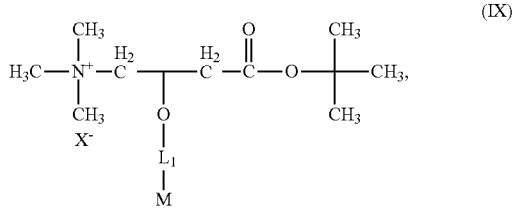

(IX)

where M is a monomeric repeating unit, $L_1$ is a linker, and $X^-$ is a counter ion associated with the cationic center.

As an example, a typical condition for removal of tert-butyl (Bu) protecting group shown in (IX) is to treat the compound with trifluoroacetic acid for 4 hours.

A general structural formula for a carnitine ester cationic monomer is shown herein as structure (X):

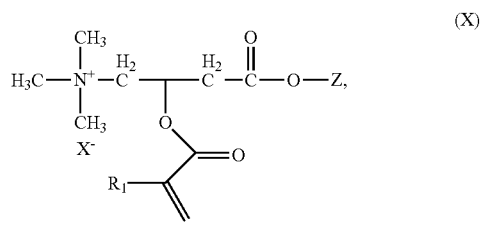

(X)

where $L_1$ is a linker, $X^-$ is a counter ion associated with the cationic center, Z is an alkyl, aryl, acyl, or silyl group, where the alkyl, aryl, acyl, or silyl group is optionally further substituted with one or more substituents, and $R_1$ is selected from the group consisting of: hydrogen, fluorine, trifluoromethyl, $C_1$-$C_6$ alkyl, and $C_6$-$C_{12}$ aryl.

A general structural formula for a carnitine ester cationic monomer is shown herein as structure (XI):

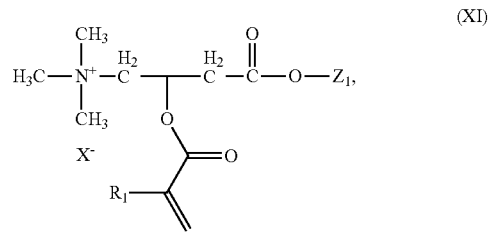

(XI)

where $X^-$ is a counter ion associated with the cationic center, $Z_1$ is a protecting group and $R_1$ is selected from the group consisting of: hydrogen, fluorine, trifluoromethyl, $C_1$-$C_6$ alkyl, and $C_6$-$C_2$ aryl.

A general structural formula for a carnitine ester cationic monomer is shown herein as structure (XII):

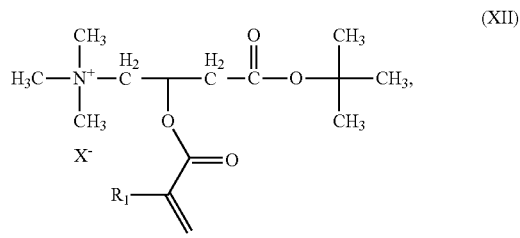

(XII)

where $X^-$ is a counter ion associated with the cationic center and $R_1$ is selected from the group consisting of: hydrogen, fluorine, trifluoromethyl, $C_1$-$C_6$ alkyl, and $C_6$-$C_{12}$ aryl.

A general structural formula for a carnitine ester cationic monomer is shown herein as structure (XIII):

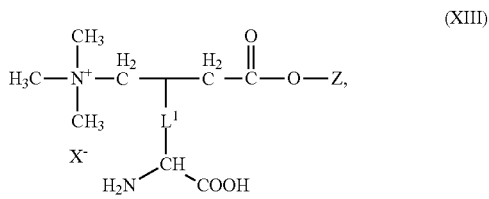

(XIII)

where $L_1$ is a linker, $X^-$ is a counter ion associated with the cationic center, and Z is an alkyl, aryl, acyl, or silyl group, where the alkyl, aryl, acyl, or silyl group is optionally further substituted with one or more substituents.

A general structural formula for a carnitine ester cationic monomer is shown herein as structure (XIV):

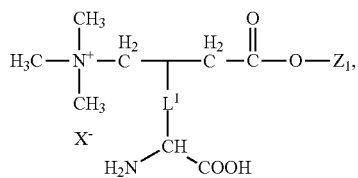
(XIV)

where $L_1$ is a linker, $X^-$ is a counter ion associated with the cationic center, and $Z_1$ is a protecting group.

A general structural formula for a carnitine ester cationic monomer is shown herein as structure (XV):

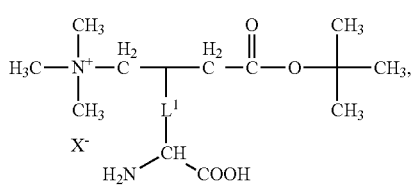
(XV)

$L_1$ is a linker, and $X^-$ is a counter ion associated with the cationic center.

Carnitine Ester Cationic Polymers

A general structural formula for a carnitine ester cationic material which is a polymer is shown herein as structure (XVI):

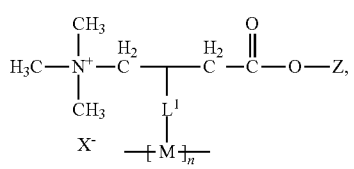
(XVI)

where M is a monomeric repeating unit, $L_1$ is a linker, n is an integer from 1 to about 10000, $X^-$ is a counter ion associated with the cationic center, and Z is an alkyl, aryl, acyl, or silyl group, where the alkyl, aryl, acyl, or silyl group is optionally further substituted with one or more substituents.

A specific structural formula for a carnitine-derived material which is a polymer is shown herein as structure (XVII):

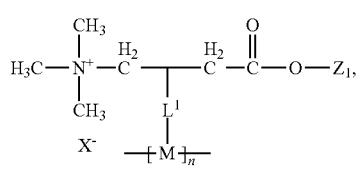
(XVII)

where M is a monomeric repeating unit, n is an integer from 1 to about 10000, $X^-$ is a counter ion associated with the cationic center, and $Z_1$ is a protecting group.

A specific structural formula for a carnitine-derived material which is a polymer is shown herein as structure (XVIII):

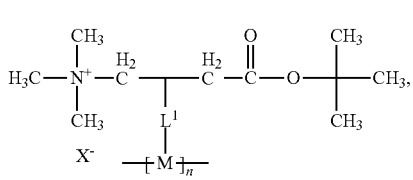
(XVIII)

where M is a monomeric repeating unit, n is an integer from 1 to about 10000, $X^-$ is a counter ion associated with the cationic center, and $L_1$ is a linker that covalently couples the carnitine molecule to the monomeric repeating unit as shown.

A general structural formula for a carnitine ester cationic material which is a polymer is shown herein as structure (XIX):

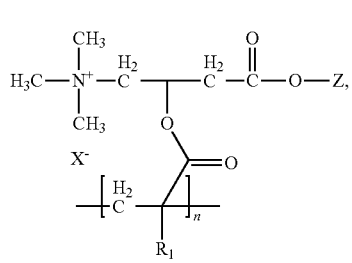
(XIX)

where n is an integer from 1 to about 10000, $X^-$ is a counter ion associated with the cationic center, Z is an alkyl, aryl, acyl, or silyl group, where the alkyl, aryl, acyl, or silyl group is optionally further substituted with one or more substituents, and $R_1$ is selected from the group consisting of: hydrogen, fluorine, trifluoromethyl, $C_1$-$C_6$ alkyl, and $C_6$-$C_{12}$ aryl.

A specific structural formula for a carnitine ester cationic material which is a polymer is shown herein as structure (XX):

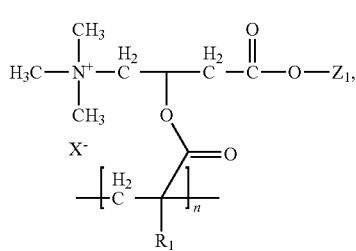
(XX)

n is an integer from 1 to about 10000, $X^-$ is a counter ion associated with the cationic center, $Z_1$ is a protecting group and $R_1$ is selected from the group consisting of: hydrogen, fluorine, trifluoromethyl, $C_1$-$C_6$ alkyl, and $C_6$-$C_{12}$ aryl.

By way of non-limiting example, $Z_1$ can be selected from, but not limited to, tert-butyl (Bu), 2-chlorotrityl (2-Cl-Trt), 2,4-dimethoxybenzyl (Dmb), 2-phenylisopropyl (2-PhiPr), 5-phenyl-3,4-ethylenedioxythenyl (phenyl-EDOTn), and a derivative of any thereof; or a benzyl group and a derivative of a benzyl group.

A specific structural formula for a carnitine ester cationic material which is a polymer is shown herein as structure (XXI):

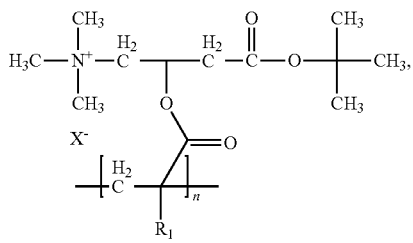

(XXI)

n is an integer from 1 to about 10000, $X^-$ is a counter ion associated with the cationic center, and $R_1$ is selected from the group consisting of: hydrogen, fluorine, trifluoromethyl, $C_1$-$C_6$ alkyl, and $C_6$-$C_{12}$ aryl.

A general structural formula for a carnitine ester cationic material which is a polymer is shown herein as structure (XXII):

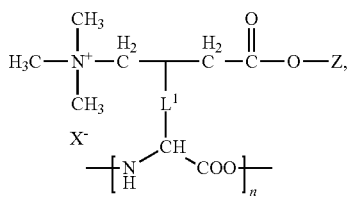

(XXII)

n is an integer from 1 to about 10000, $X^-$ is a counter ion associated with the cationic center, $L_1$ is a linker that covalently couples the carnitine molecule to the monomeric repeating unit, and Z is an alkyl, aryl, acyl, or silyl group, where the alkyl, aryl, acyl, or silyl group is optionally further substituted with one or more substituents.

A specific structural formula for a carnitine ester cationic material which is a polymer is shown herein as structure (XXII):

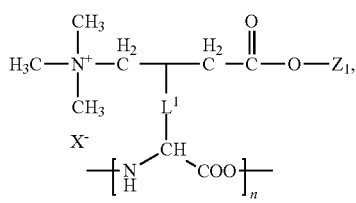

(XXIII)

n is an integer from 1 to about 10000, $L_1$ is a linker that covalently couples the carnitine molecule to the monomeric repeating unit, $X^-$ is a counter ion associated with the cationic center, and $Z_1$ is a protecting group.

A specific structural formula for a carnitine ester cationic material which is a polymer is shown herein as structure (XXIV):

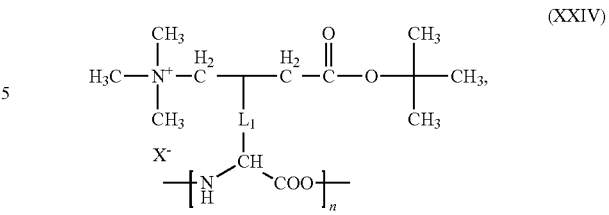

(XXIV)

n is an integer from 1 to about 10000, $L_1$ is a linker that covalently couples the carnitine molecule to the monomeric repeating unit, and $X^-$ is a counter ion associated with the cationic center.

A specific structural formula for a carnitine ester cationic material having a reactive functional terminal group, wherein the material is a polymer is shown herein as structure (XXVIII):

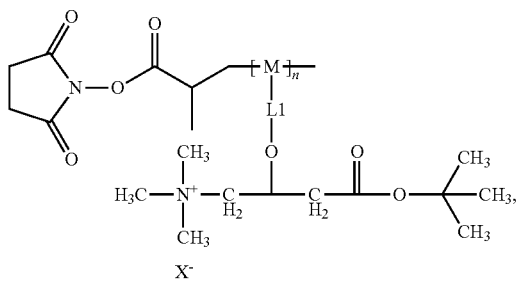

(XXVIII)

M is a monomeric repeating unit, n is an integer from 1 to about 10000, $L_1$ is a linker that covalently couples the carnitine molecule to the monomeric repeating unit, and $X^-$ is a counter ion associated with the cationic center.

A specific structural formula for a carnitine ester cationic material having a reactive functional terminal group wherein the material is a polymer is shown herein as structure (XXIX):

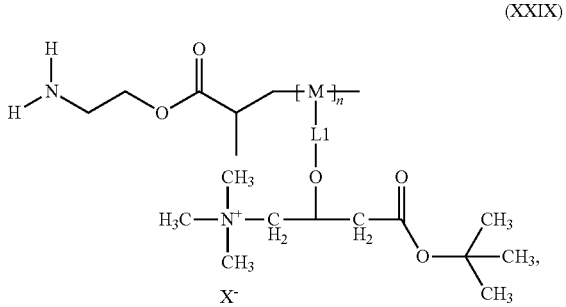

(XXIX)

M is a monomeric repeating unit, n is an integer from 1 to about 10000, $L_1$ is a linker that covalently couples the carnitine molecule to the monomeric repeating unit, and $X^-$ is a counter ion associated with the cationic center.

Methods of Synthesis of Carnitine Ester Materials

Provided according to aspects of the present invention is a synthesis protocol to obtain a novel carnitine ester material, exemplified in Example 5 herein.

Carnitine ester materials provided by the present invention are useful in various ways such as, but not limited to, use in synthesis of carnitine derived zwitterionic materials, as antimicrobial polymers, and as condensing/complexing polymer reagents for negatively charged proteins, genes or polymers.

Assemblies

Assemblies, such as liposomes, micelles, polymersomes and other particle assemblies are generated using well-known standard methods, such as described in Liao J et al., Recent advances in formation, properties, and applications of polymersomes, Curr Pharm Des. 2012; 18(23):3432-41; Milller L K et al., Natural liposomes and synthetic polymeric structures for biomedical applications, Biochem Biophys Res Commun. 2015, 468(3):411-8; and Lu Y et al., Polymeric micelles and alternative nanonized delivery vehicles for poorly soluble drugs, Int J Pharm. 2013, 453(1): 198-214.

The term "liposome" refers to a bilayer particle of amphipathic lipid molecules enclosing an aqueous interior space. Liposomes are typically produced as small unilammellar vesicles (SUVs), large unilammellar vesicles (LUVs) or multilammellar vesicles (MLVs). A therapeutic and/or diagnostic agent can be associated with liposomes by encapsulation in the aqueous interior space of the liposomes, disposed in the lipid bilayer of the liposomes and/or associated with the liposomes by binding, such as ionic binding or association by van der Waals forces.

Liposomes, micelles, polymersomes and other particle assemblies according to aspects of the invention are generally in the range of about 1 nanometer-1 micron in diameter although they are not limited with regard to size.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003; L. V. Allen, Jr. et al., Ansel's Pharmaceutical Dosage Forms and Drug Delivery Systems, 8th Ed., Philadelphia, Pa.: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

Pharmaceutically acceptable carriers and formulation of pharmaceutical compositions are known in the art, illustratively including, but not limited to, as described in Remington: The Science and Practice of Pharmacy, 21 Ed., Lippincott, Williams & Wilkins, Philadelphia, Pa., 2006; and Allen, L. V. et al., Ansel's Pharmaceutical Dosage Forms and Drug Delivery Systems, 8$^{th}$ Ed., Lippincott, Williams & Wilkins, Philadelphia, Pa., 2005.

The singular terms "a," "an," and "the" are not intended to be limiting and include plural referents unless explicitly stated otherwise or the context clearly indicates otherwise.

Embodiments of inventive compositions and methods are illustrated in the following examples. These examples are provided for illustrative purposes and are not considered limitations on the scope of inventive compositions and methods.

EXAMPLES

Example 1

Materials

L-carnitine hydrochloride (>98%), anhydrous N,N-Dimethylformamide (DMF, 99.8%), hydroquinone (99%), triethylamine (TEA, 99.5%), anhydrous dichloromethane (DCM, 99.8%), anhydrous Diethyl ether (99%), copper(I) bromide (99.9%), bromoisobutyryl bromide (BIBB 98%), 11-mercapto-1-undecanol (97%), 2,2'-bipyridine (BPY 99%), and activated charcoal (DARCO, −100 particle size) were purchased from Sigma-Aldrich Chemical Company, Milwaukee. Anhydrous Methanol (99%) and acryloyl chloride (>96%) were obtained from Alfa Aesar, Thermo Fisher Scientific. Alcohol (200 proof) was purchased from Decon Laboratories, Inc.

Synthesis and Purification of the L-carnitineMA Monomer

Synthesis of the L-carnitineMA monomer was achieved using a one-step reaction, the scheme for which is shown in FIG. 1. Briefly described, 1.97 g L-carnitine hydrochloride (10 mmol) and 100 mg hydroquinone were added into 25 ml anhydrous dimethylformamide (DMF) in a flask purged with nitrogen. The mixture was heated to 40° C. and stirred for 10 mins. Then 2.43 ml acryloyl chloride (30 mmol) was dropped into the solution and the temperature was raised to 80° C. to react for 3 h. During the reaction, the flask was connected to a tube that leads to a liquid-seal bottle filled with triethylamine (TEA) to absorb excessive hydrogen chloride (HCl) from the reaction. The starting material L-carnitine hydrochloride gradually dissolved and the solution turned clear and brown.

It is critical to select the right solvent for the one-step reaction to obtain L-carnitineMA monomer. Acryloyl chloride has to be dissolved in a non-protic solvent to preserve its reactivity. L-carnitine on the other hand is hydrophilic and can hardly be dissolved in most non-protic solvents such as acetonitrile and DCM, as shown in Table 1. By increasing the temperature, L-carnitine hydrochloride can be partially dissolved in DMF and dimethyl sulfoxide (DMSO). Since DMSO drastically reacted with acryloyl chloride through Swern-oxidation, DMF was chosen as the solvent.

TABLE 1

Solubility of L-carnitine hydrochloride and L-carnitine inner-salt at 80 mg/ml in different solvent at 40° C., and 80° C.
(No: not soluble; partial: partially soluble; Yes: soluble)

| Chemicals | T(°C.) | DCM | THF | EA | CHCl$_3$ | Acetone | ACN | DMF | DMSO |
|---|---|---|---|---|---|---|---|---|---|
| L-carnitine hydrochloride | 40 | No | No | No | No | No | No | No | partial |
|  | 80 | No | No | No | No | No | No | partial | Yes |
| L-carnitine inner-salt | 40 | No | No | No | No | No | No | No | No |
|  | 80 | No | No | No | No | No | No | No | partial |

The reaction temperature was chosen at 80° C. since L-carnitine hydrochloride can be partially dissolved in solvent DMF at this temperature to facilitate the reaction. In addition, maintaining high temperature (40° C. or above) is critical since hydroquinone was oxidized to benzoquinone, which is a polymerization inhibitor, at lower temperatures and does not react with acryloyl chloride, leading to side products. The data generated here show that at room temperature hydroquinone reacted with acryloyl chloride significantly (calculated Mw $C_{12}H_{10}O_4$+H was 219.7, confirmed by mass spectroscopy of an m/z of 220.1).

In a typical reaction between a hydroxy group and acryloyl chloride, TEA is often used in such reaction mixtures as the deacid reagent to increase reaction efficiency. However, TEA cannot be used in synthetic reaction systems of the present invention because: (1) it turned the L-carnitine from hydrochloride form to inner-salt form, which was totally insoluble in DMF even at 80° C., see Table 1; and (2) at high temperature, the acryloyl chloride reacted with TEA significantly and produced side products that complicated the purification procedure.

After the single-step reaction described above, the rough product was purified as follows. The majority of hydrogen chloride generated and the excess amount of acryloyl chloride was removed under vacuum at room temperature by stirring the reaction solution. Then the resulting mixture was placed at −20° C. overnight. Unreacted L-carnitine hydrochloride was precipitated and removed by filtration. The resulting solution was further treated by anhydrous TEA where the L-carnitineMA monomer product, triethylamine hydrochloride and certain colored impurities were precipitated. The precipitate was washed with dichloromethane (DCM) to remove triethylamine hydrochloride and was vacuum-dried. To remove the colored impurity, the obtained product was dissolved in anhydrous methanol stirred with activated charcoal for 2 h at 40° C. The supernatant was obtained by centrifugation, precipitated in diethyl ether and dried in vacuum. L-carnitineMA monomer in the form of light-yellow powder was obtained at the optimized yield of ~43%.

Characterization of L-carnitineMA Monomer

The nuclear magnetic resonance (NMR) spectrum of L-carnitineMA was measured using a Varian Mercury-400 MHz NMR, using the $D_2O$ as the solvent. The areas under the peak were calculated using mestrec23 software. The mass spectrometry was conducted on a Water Micromass ZQ ion trap mass spectrometer in methanol as the solvent.

Figure 2:
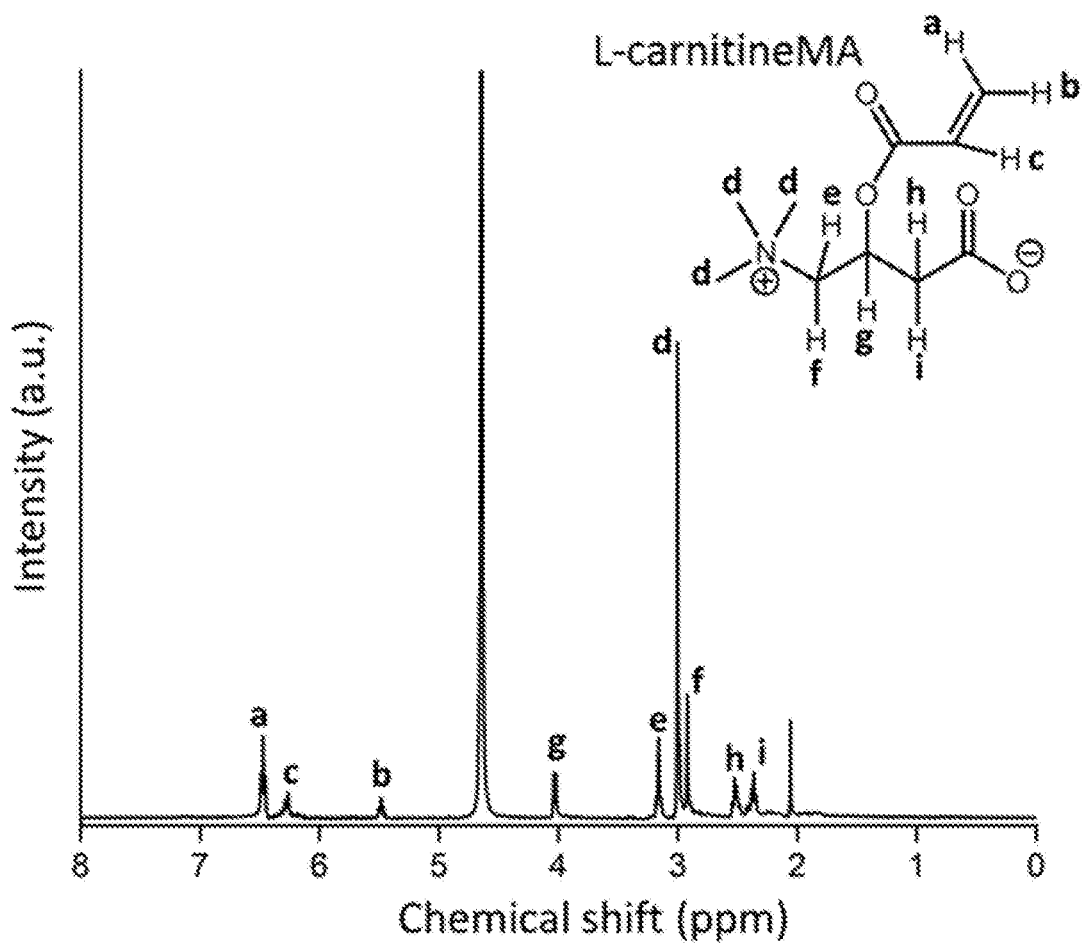
FIG. 2 shows $H^1$ NMR characterization of L-carnitineMA monomer.
Figure 6:
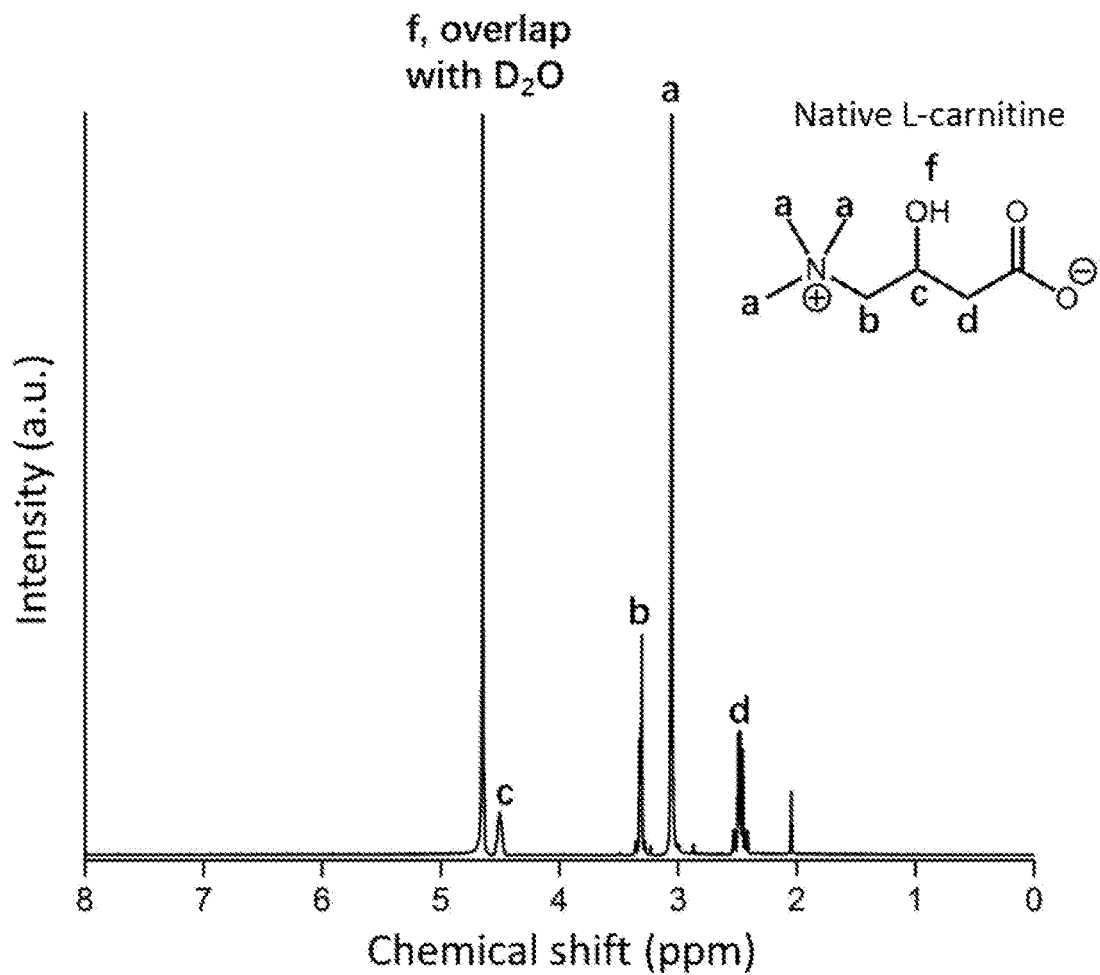
FIG. 6 shows $H^1$ NMR characterization of L-carnitine.

As shown in FIG. 2, the structure of L-carnitineMA monomer was confirmed with NMR. Compared with NMR analysis of unreacted L-carnitine shown in FIG. 6, it can be seen that L-carnitineMA monomer showed three new NMR peaks (a, b and c) corresponding to the three hydrogens on the double bond structure. The area ratio of peak d (9 hydrogens from the quaternary ammonium structure) and peak b (1 hydrogen from the double bond structure) was 8.87, indicating no polymerization occurred during the monomer synthesis. The mass spectrometer further confirmed the success of synthesis by giving an m/z of 216.2 for the L-carnitineMA monomer (calculated Mw for L-carnitineMA+H was 216.4).

Preparation of L-carnitineMA Polymer Brush Coating on Gold Substrate

SPR glass chip coated with a surface plasmon active gold layer was purchased from Institute of Photonics and Electronics, Czech Academy of Sciences, Czech Republic. The gold surface was washed with DI water and pure ethanol, and then it was placed in an O-zone cleaner and heated for 20 mins. After cleaning, the chip was soaked overnight in the pure ethanol containing 1 mM ATRP initiator ω-mercaptoundecyl bromoisobutyrate. The gold substrate was then rinsed with pure ethanol followed by tetrahydrofuran (THF) and dried in a stream of nitrogen. The L-carnitineMA polymers were grown onto the gold substrate by atom transfer radical polymerization (ATRP). Briefly, DI water and DMF were purged with nitrogen for 15 mins to remove oxygen. 21.4 mg CuBr and 46.25 mg 2,2′-Bipyridine (BPY), as well as the cleaned substrate, were added into a reaction tube treated with three vacuum/nitrogen cycles. 216 mg L-carnitineMA monomer (1 mmol) was added into another reaction tube treated with three vacuum/nitrogen cycles. 5 ml mixed solvent (DI water/DMF 2:1 volume ratio) was added to both tubes and the L-carnitineMA monomer solution was transferred to the tube containing the gold chip using a syringe. The tube was tightly sealed and the ATRP reaction was carried out with gentle stirring at room temperature for 3 h. After the reaction, the L-carnitineMA polymer coated substrate was immersed in DI water to remove unreacted L-carnitineMA monomer and other small molecules before the test.

Coating Thickness Characterization

After ATRP, the polymer brush thickness was measured by surface ellipsometry and atomic force microscope (AFM). The surface ellipsometry was performed on an ellipsometer (α-SETM, J. A. Woollam Co., Inc.) and the thickness was calculated by the average of three measurements of different coating sites with an assumed gold surface refractive index of 1.45. The AFM imaging of bare gold substrate and L-carnitineMA polymer brush-coated gold substrate were conducted on a Dimension 3100 AFM from VEECO. Samples were vacuum dried before imaging. An L-carnitineMA polymer brush coating was gently scratched with a sharp lancet to expose the coating section for thickness measurement. The coating thickness and morphology were measured in the air through the tapping mode using silicon probes (VEECO) with a nominal frequency of 150 kHz. The AFM images were analyzed using Nanoscope software version 5.12 (VEECO).

It was found that the reaction temperature (room temperature or 40° C.) and the reaction time (3 h or longer) did not affect the coating thickness significantly (differences less than 2%). The reaction solvent or mixed solvent, however, had a profound impact on the coating thickness as shown in Table 2.

TABLE 2

L-carnitineMA polymer coating thickness on gold substrate obtained from different ATRP reaction solvent (average ± standard deviation, n = 3)

| solvent | Water | DMF | Methanol | Film thickness (nm) |
| --- | --- | --- | --- | --- |
| Volume ratio | 1 | 0 | 0 | 8.5 ± 1.3 |
| | 1 | 1 | 0 | 16.4 ± 2.8 |
| | 1 | 0 | 1 | 5.7 ± 1.2 |
| | 0 | 0 | 1 | 2.3 ± 0.5 |
| | 2 | 1 | 0 | 23.0 ± 3.8 |
| | 2 | 0 | 1 | 7.3 ± 1.9 |
| | 1 | 1 | 1 | 6.5 ± 2.2 |

It appeared that the use of methanol in the mixed solvent decreased the obtained polymer brush thickness. Water/DMF system was more suitable to grow L-carnitineMA polymer films, and at 2:1 water/DMF volume ratio, the film thickness reached 23.0±3.8 nm (average±standard deviation, n=3). This thickness is comparable to 26.6±0.5 nm of PCBMA brush coating, which shows superior anti-fouling performance.

Figure 3A:
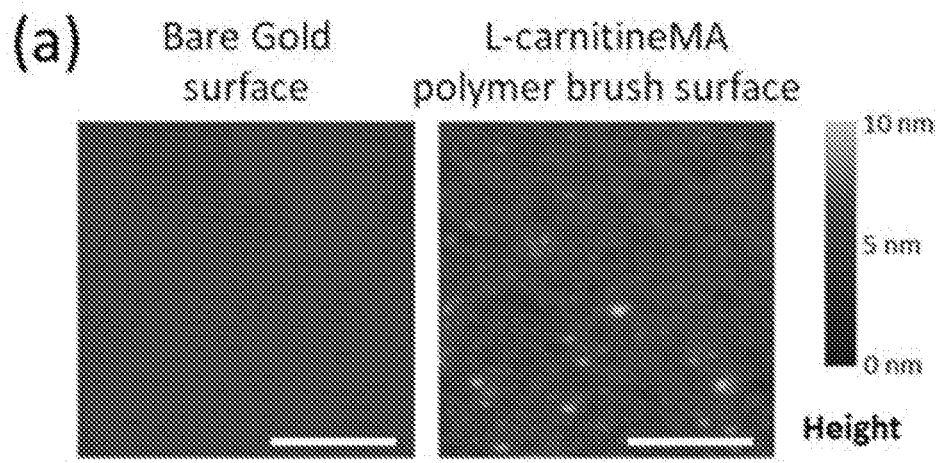
FIG. 3A shows atomic force microscopy (AFM) images comparing a bare gold surface with an L-carnitineMA polymer brush surface.
Figure 7:
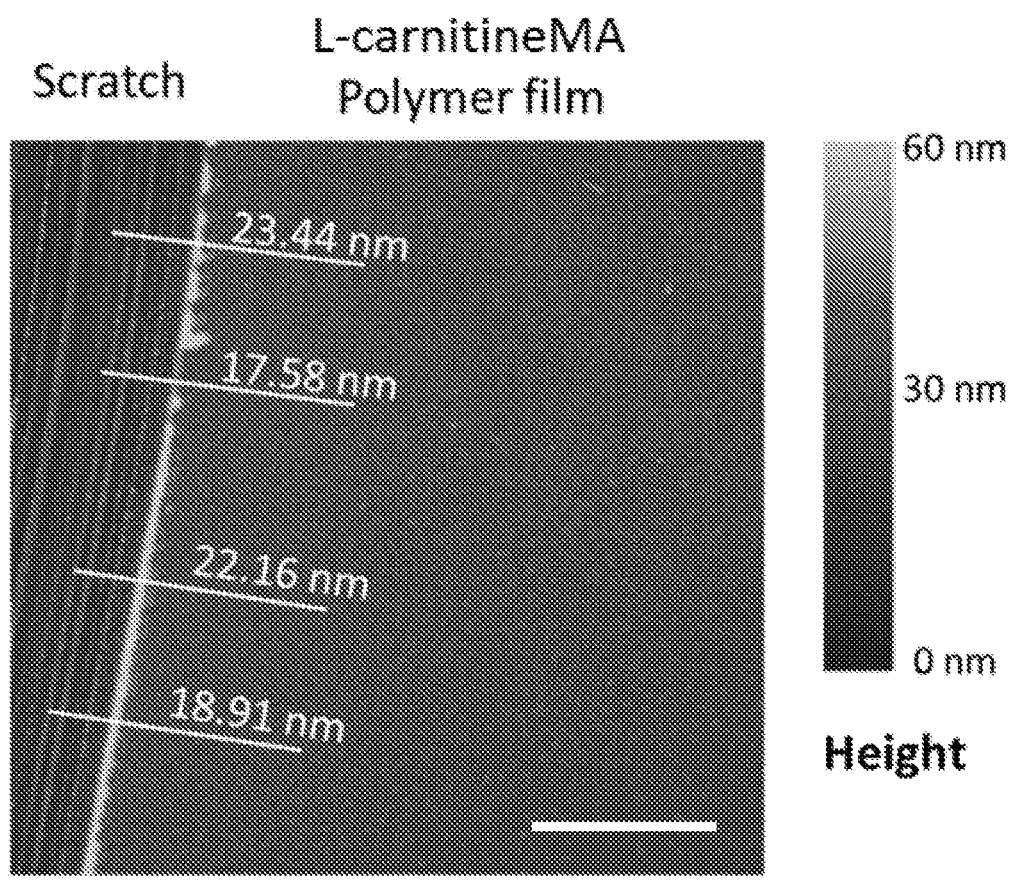
FIG. 7 is an image showing measurement of scratch depth on the L-carnitineMA polymer brush surface, scale bar=10 μm.

The morphology of L-carnitineMA polymer brush surface was significantly different from bare gold surface as visualized by the taping mode of atomic force microscope (AFM), see FIG. 3A. The thickness of L-carnitineMA polymer brush surface was also measured by AFM. A shallow scratch was made on the L-carnitineMA polymer brush surface using a sharp lancet. By measuring the depth of the scratch, the polymer brush thickness was calculated, see FIG. 7, to be 20.5±4.6 nm (average±standard deviation, n=4), in agreement with the thickness value measured by surface ellisometry.

Measurement of Protein Adsorption by an SPR Sensor

The protein absorption on the bare gold substrate, the L-carnitineMA polymer brush-coated substrate, and the PCBMA polymer brush-coated substrate were measured using a surface plasmon resonance (SPR) sensor custom-built by Institute of Photonics and Electronics, Czech Academy of Sciences, Czech Republic. The tested chips were attached to the base of the prism. A four-channel flow cell with four independent parallel flow channels was used to contain liquid samples during experiments. PBS buffer at 50 µl/min and 25° C. was first used to obtain a stable baseline. Fibrinogen (negatively charged, from bovine plasma, Sigma) and lysozyme (positively charged, from chicken egg white, Sigma) solutions of 1.0 mg/mL in PBS (0.15 M, pH 7.4) flowed over the surfaces at a flow rate of 0.05 mL/min for 10 min followed by flowing PBS to remove any loosely bound proteins. A surface-sensitive SPR detector was used to monitor protein-surface interactions in real time. Wavelength shift between the baselines before and after protein injection was used to measure the non-specific protein adsorption (surface protein concentration in mass per unit area) on the surface. For bare-gold SPR substrates, a 1 nm wavelength shift starting at a resonant wavelength of 750 nm represents 17 ng/cm$^2$ of absorbed proteins, see J. Homola, Surface Plasmon Resonance Based Sensors, Springer-Verlag, 2006. For L-carnitineMA polymer brush surface of 23 nm, a calibrator factor of 1.31 was calculated based on existing protocol described in detail in Cao Z, et al., Angew. Chem. Int. Ed., 2011, 50:6102-6104. Thus, for this specific L-carnitineMA polymer coated chip, a 1 nm shift in resonant wavelength represents 22.3 ng/cm$^2$ of protein coverage.

Figure 3B:
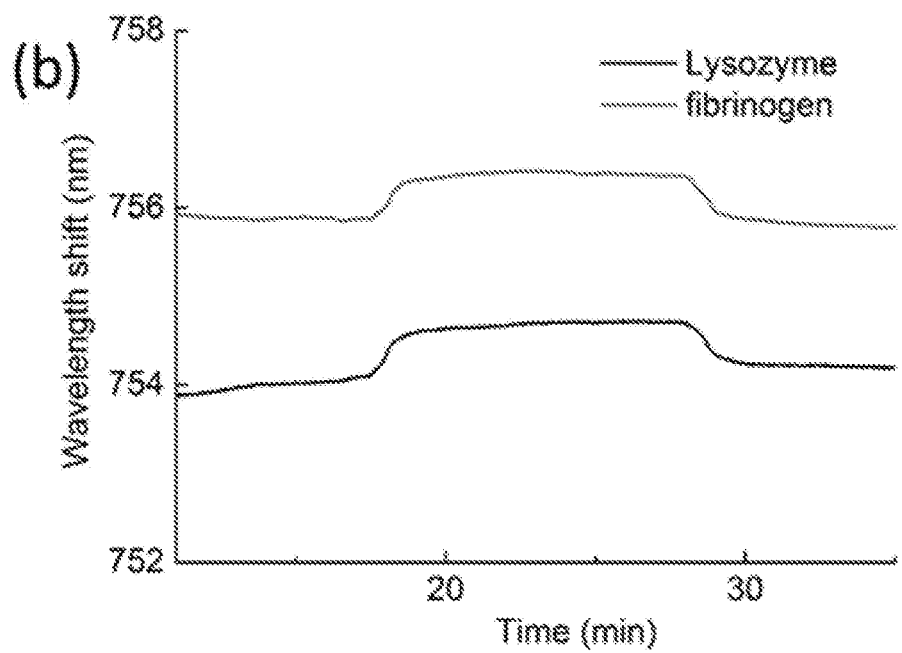
FIG. 3B is a graph showing adsorption of 1 mg/mL fibrinogen and lysozyme in PBS buffer on L-carnitineMA polymer brush coated gold surface as determined by SPR.

Undetectable adsorption (<0.3 ng/cm$^2$) of both fibrinogen and lysosome was observed as shown in FIG. 3B. The results indicate that the obtained L-carnitineMA polymer coated surface displayed "super-low-fouling" against protein binding that is comparable to PCBMA (<0.3 ng/cm$^2$) coatings. Super-low fouling is defined by being able to resist protein adsorption down to <5 ng/cm$^2$, which is desirable to inhibit platelet adhesion for blood compatibility. As a reference, a monolayer of protein binding resulted in a sensor response of 100-500 ng/cm$^2$.

Figure 5A:
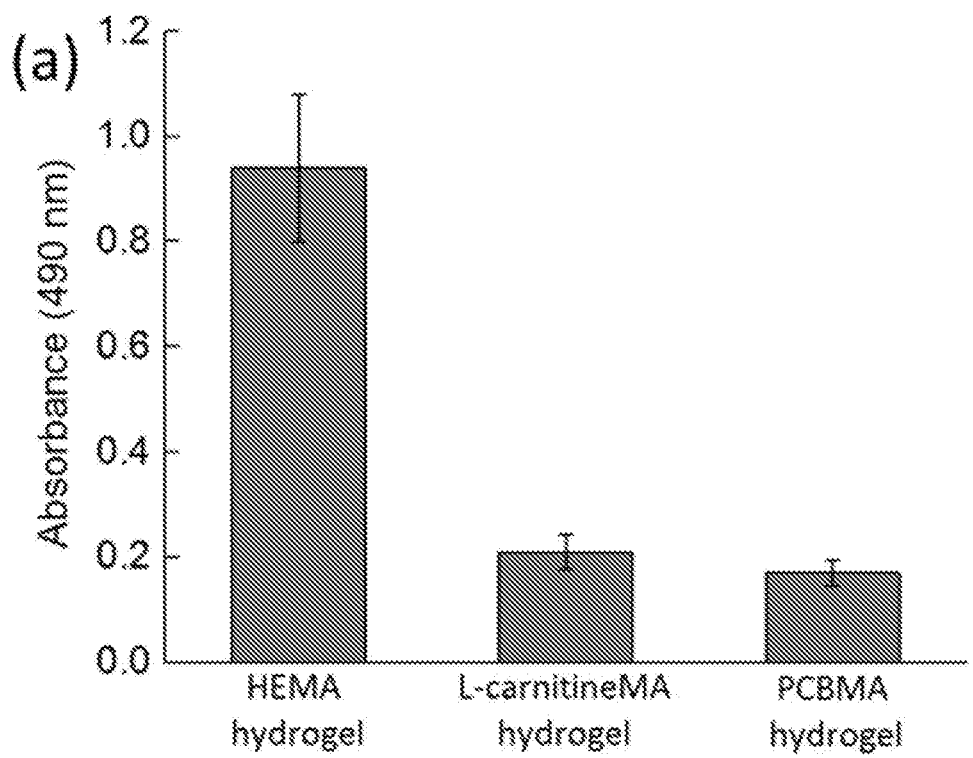
FIG. 5A is a graph showing results of a protein binding test on HEMA, poly-L-carnitineMA and PCBMA hydrogel.
Figure 5B:
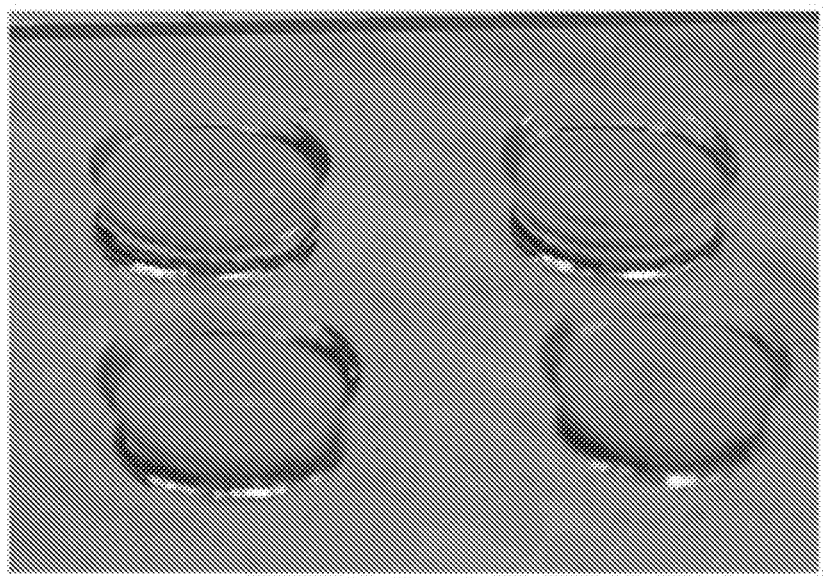
FIG. 5B is an optical image of poly-L-carnitineMA hydrogel.

A hydrogel network, see FIG. 5B, using L-carnitineMA monomer and commercial N,N'-Methylenebisacrylamide (MBAA) crosslinker through UV initiation was prepared and tested for anti-fouling properties.

The L-carnitineMA hydrogel was fabricated by UV initiation of L-carnitineMA monomer solution of 50% (weight ratio) in the presence of 0.2% UV initiator 2-Hydroxy-4'-(2-hydroxyethoxy)-2-methylpropiophenone (1-2959) and 5% crosslinker N,N'-Methylenebisacrylamide (MBAA). The pre-gel solution was filled in the space between two glass slides separated by a Teflon spacer with 1 mm thickness. The hydrogels were equilibrated in DI water to remove unreacted small molecules. Hydrogel samples were tailored into a disc shape (5 mm in diameter and 1 mm in thickness) using a punch for further evaluation.

The anti-fouling property of the L-carnitineMA derived hydrogel in resisting protein binding was evaluated by enzyme-linked immunosorbent assay (ELISA) using the human fibrinogen as the model protein.

To measure the human fibrinogen (Fg, Sigma-Aldrich) adsorption on PCBMA (positive control), PHEMA (negative control) and L-carnitineMA hydrogel, the hydrogel samples were incubated with 1 mg/ml Fg in a 24-well plate for 10 minutes at room temperature, followed by 5 washes with PBS buffer. L-carnitineMA hydrogels were then incubated with 1 mg/ml bovine serum albumin solution for 10 minutes at room temperature with 5 times wash again with PBS buffer. The tested hydrogel samples were then transferred to new wells. They were next incubated with a 1:200-dilution of horseradish peroxidase (HRP)-conjugated anti-fibrinogen in PBS for 10 minutes, followed by another 5 washes with the same buffer. After the fifth wash, the tested hydrogels were transferred to new wells and SIGMAFAST OPD was added to each well at 30-second intervals. The samples were incubated in the OPD solution for 30 minutes away from light. The supernatant was removed from each test well, transferred to a 96-well plate, and its absorbance at 490 nm was measured. All samples were measured in triplicate.

Results indicated that the L-carnitineMA hydrogel showed better anti-fouling property compared to poly-(Hydroxyethyl)methacrylate (PHEMA) hydrogel (negative control), and was able to achieve a similar anti-fouling level as the commonly used PCBMA hydrogel, see FIG. 5A.

Microorganism Adhesion Test

The L-carnitineMA polymer brush coating was further challenged in a microorganism adhesion test using *E. coli* K12 as the model bacterium.

For bacteria culture, *E. coli* K12 was cultured overnight at 37° C. on Luria-Bertani (LB) agar plates. One colony was picked and transferred to the culture in 25 mL of LB medium (20 g/L) overnight under 37° C. at 300 rpm shaking rate. The bacteria culture was used to inoculate a second culture in 150 ml of LB medium. The new culture was continuously shaken under 37° C. until it reached an optical density of 0.9 at 600 nm. The obtained bacteria were collected by centrifugation at 4400 rpm for 5 min. The bacteria were then washed with sterile PBS for three times and diluted to a concentration of 10$^8$ cell/ml for the adhesion experiments.

The bare gold surface, gold surface coated with L-carnitineMA polymer and PCBMA polymer were placed in the bacterial suspension (10$^8$ cells/ml) for 0.5 h followed by a gentle wash with PBS to remove loosely bound bacteria.

After bacteria incubation with the substrates, the substrates were removed and immersed in a fix solution of 2.5% glutaraldehyde, 2% paraformaldehyde in 0.1 M sodium phosphate buffer. Then the substrate was dehydrated in a gradient ethanol series and dried in vacuum. Before SEM imaging, the substrate sample was coated with a nano-gold layer for 20 s using an SEEVac Conductive IV sputter coater. The adhered bacteria were imaged using a JSM-6510LV SEM at 5 µm magnification and bacteria adhesion density was calculated by counting the bacteria number per 900 µm$^2$.

Figure 4A:
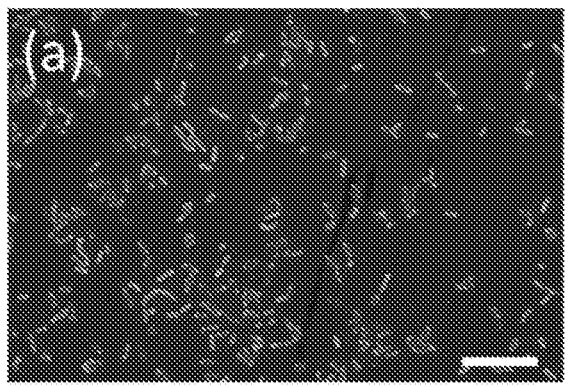
FIG. 4A is an image showing an E. coli adhesion test on a bare gold surface.
Figure 4C:
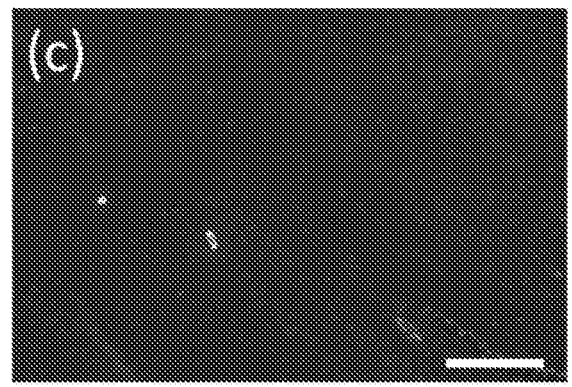
FIG. 4C is an image showing an E. coli adhesion test on an L-carnitineMA polymer brush coating.
Figure 4B:
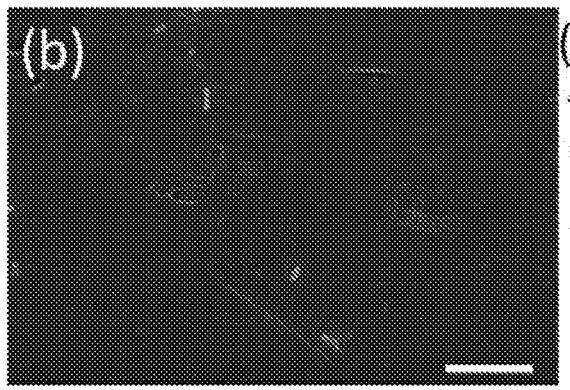
FIG. 4B is an image showing an E. coli adhesion test on a PCBMA polymer brush coating.
Figure 4D:
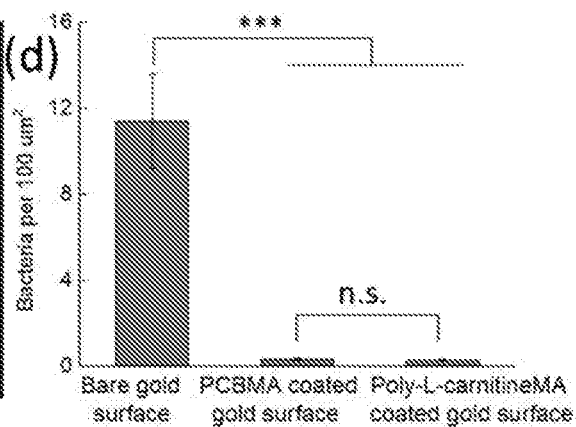
FIG. 4D is a graph showing calculated bacteria adhesion density by comparison of the number of bacteria per 100 square microns on a bare gold surface, a PCBMA coated gold surface, and a poly-L-carnitineMA coated gold surface, Statistical analysis: one-way ANOVA with Bonferroni multi-comparison, ***: $p<0.0001$, n.s.: no significant differences, $p>0.5$, Scale bar=10 μm.

SEM images, see FIGS. 4A, 4B, and 4C showed that the L-carnitineMA polymer brush surface greatly reduced the bacteria adhesion (0.28 f 0.03 bacteria per 100 µm$^2$ (average±standard deviation, n=6)), as compared to the uncoated bare gold surface (11.4±2.2 bacteria per 100 µm$^2$). The bacteria adhesion on PCBMA was 0.32±0.05 bacteria per 100 µm$^2$, and there was no significant difference between the PCBMA coated surface and L-carnitineMA polymer coated surface in bacteria adhesion density at p<0.0001, see FIG. 4D. Results indicate that the L-carnitineMA polymer has the same superior anti-fouling capability against bacteria adhesion as the state-of-the-art zwitterionic polymer PCBMA.

Example 2

Synthesis and Purification of a NHS Ester Terminated Carnitine-Derived Zwitterionic Polymer NHS ester terminated carnitine-tBu ester polymer was treated with trifluoracetic acid to remove tBu group, precipitated in ethyl ether and dried under vacuum condition to obtain NHS ester termineated carnitine derived zwitterionic polymer.

Synthesis and Purification of Amino Group Terminated Zwitterionic Carnitine-Derived Zwitterionic Polymer Amino group terminated carnitine-tBu ester polymer was treated with trifluoracetic acid to remove tBu group, precipitated in ethyl ether and dried under vacuum condition to obtain NHS ester termineated carnitine derived zwitterionic polymer.

Synthesis and purification of carnitine-derived zwitterionic polymer-protein conjugate.

Synthesis and purification of carnitine-derived zwitterionic polymer-insulin conjugate.

Conjugation of carnitine polymer and insulin will be carried out by reacting NHS ester groups of the polymer with available amine groups on the protein. Typically, insulin (1 mg/ml) will be dissolved in 0.1 M Na2CO3 buffer. Pre-dissolved NHS ester terminated carnitine-derived zwitterionic polymer will be added into the insulin solution at polymer: insulin molar ratio=1.2:1, and the reaction mixture will be stirred at 700 rpm for one hour in ice bath to obtain rough product. After the reaction, the buffer will be adjusted to pH 7.4 by HCl. To purify the obtained carnitine-derived zwitterionic polymer-insulin conjugate, the rough product will be placed in a dialysis kit (e.g., 6-8 kDa, MWCO, Sigma-Aldrich) against PBS. The MW cut off will be chosen to retain the polymer-insulin conjugates, but allow both free insulin and unconjugated polymer to go through. The purified polymer-insulin sample will be desalted using PD-10 column and lyophilized for storage.

Synthesis of Carnitine-Derived Zwitterionic Polymer-Chemo Drug Conjugate

Synthesis of Carnitine-Derived Zwitterionic Polymer-Paclitaxel Conjugate.

853 mg (1 mmol) Paclitaxel and 280 ul (2 mmol) triethylamine will be dissolved in 5 ml DMF with ice bath. 255 ul (3 mmol) acryloyl chloride will be then added into the mixture and continue reaction for 2 hours. Precipitates will be filtrated and excess acryloyl chloride will be removed under reduced pressure. Raw product will be obtained via precipitating mixture in ethyl ether. The product will be washed with cold chloroform 3 times and dried under vacuum to obtain paclitaxel monomers (i.e., paclitaxel with hydroxyl groups, e.g., at C2' and/or C7, modified with polymerisable double bonds).

Paclitaxel monomer, carnitine-tBu monomer and benzyl peroxide will be dissolved in DMF at 60° C. and kept stirring for 1 hour. Resulting copolymers will be obtained via precipitating in ethyl ether to remove paclitaxel monomer. The raw product will be treated with trifluoracetic acid to remove tBu group and precipitated in ethyl ether and dried under vacuum condition. The obtained product will be dialyzed in water to remove trace monomers and impurities. Final product of carnitine-derived zwitterionic polymer-paclitaxel conjugate will be obtained after lyophilization.

Example 3

Synthesis and Purification of Lipid-Carnitine Polymer Conjugate

DSPE-Carnitine Polymer Conjugate 1,2-Distearoyl-sn-glycero-3-phosphoethanolamine (DSPE, Genzyme Pharmaceuticals) will be used as received. In a typical reaction, 0.73 g of NHS ester terminated carnitine tBu polymer (MW for Polymer is 5K) and 0.31 g of DSPE will be stirred in 60 mL choloform/8.6 mL DMF mixed solvents in the presence of 142 μL triethylamine (TEA) for 5 days. The reaction mixture will be then evaporated and precipitated in ethyl ether. The precipitates will be extracted by acetonitrile and filtered to remove unconjugated DSPE. The filtrate containing DSPE-carnitine polymer conjugate and unconjugated carnitine polymer will be dried, treated by trifluoroacetic acid (TFA) for 4 h, precipitated in ethyl ether, and vacuum dried. The resulting product containing DSPE-carnitine polymer conjugate and unconjugated carnitine polymer will be neutralized in 200 mM phosphate buffer (pH=8) with 20 mM hydroxylamine, and ultrafiltrated (30K MW cutoff, Amicon Ultra-15, Millipore, Billerica, Mass.) in PBS, and later in water repeatedly. The obtained lipid-polymer conjugate will be freeze-dried for further use.

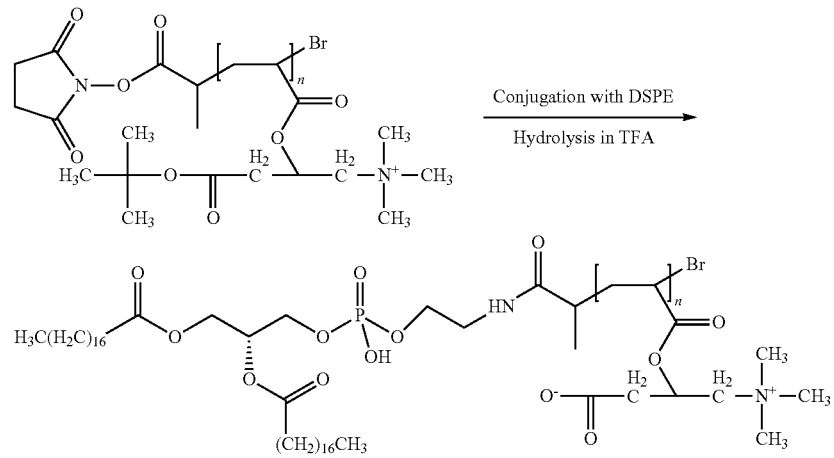

Example 4

Synthesis and Purification of Lipid-Carnitine Polymer Conjugate

PLGA-Carnitine Polymer Block Copolymer

The conjugation process will be via NHS/EDC chemistry. Briefly, 3.2 g COOH terminated PLGA (0.20 dl/g), 86.4 mg NHS and 147.2 mg EDC will be reacted in 6 ml methylene chloride for 4 h at room temperature. Then, 5 ml ethyl ether will be added to obtain white precipitates. The resulting PLGA-NHS will be washed with cold ethyl ether/methanol mixture (2/1, V/V) to remove any NHS and EDC residuals, then vacuum-dried before use. 925 mg NH2 terminated carnitine tBu ester polymer and 1.68 g PLGA-NHS will be conjugated in the presence of 50 µl triethylamine in 7 ml acetonitrile at 60° C. for 20 h. The resulting PLGA-carnitine-tBu block polymer will be precipitated in cold methanol. Unconjugated polymer could dissolve in cold methanol and will be removed by repeating the washing cycle. Then PLGA-co-Carnitine-tBu polymer will be treated with TFA for 1 h to remove tBu ester groups. The resulting PLGA-co-Carnitine polymer will be precipitated into ethyl ether repeatedly and dried in vacuum before use.

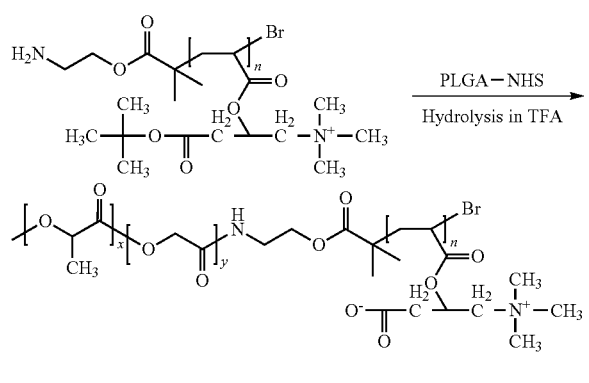

Example 5

Example Procedure for Generation of L-carnitine Ester Materials

In this example, synthesis of a carnitine ester material, acrylic carnitine tert-butyrate, is described. This synthetic scheme can be modified, for example by use of alternate starting materials to produce other carnitine ester materials.

Step 1—Synthesis of tert-butyl-3, 4-epoxybutyrate (2) from tertbutyl 3-butenoate (1)

To a solution of 0.84 g (6 mmoles) tertbutyl 3-butenoate 1 in 10 ml of chloroform was added dropwise, with cooling and stirring, a solution of 1.82 g (9 mmoles) of m-chloroperbenzoic acid in 25 ml of chloroform. The solution was allowed to stand at 40° C. for 20 hours, using TLC to monitor whether the reaction has complete. The resulting precipitate was removed by filtration, and the filtrate was stirred with 30 ml of freshly prepared aqueous 10% sodium sulfite solution for 30 min (negative starch-iodide test). Then add 5% sodium bicarbonate solution until there is no bubble formed. Collect the organic phase and dry over anhydrous magnesium sulfate until the solution becomes clear. Remove the solvent of the filtrate by rotary vacuum until colorless liquid. The product was distilled as a colorless liquid at reduced pressure, bp 40-42° C. at 0.3 mm Hg.

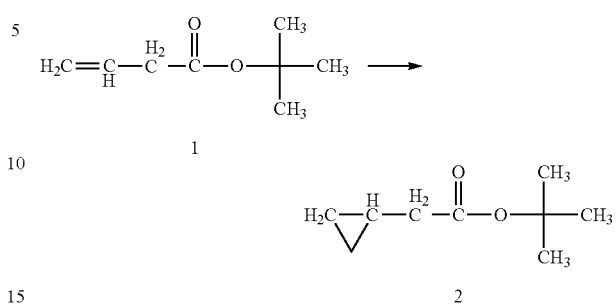

Step 2—Synthesis of Carnitine tert-butyrate (3) from tert-butyl-3, 4-epoxybutyrate (2)

A mixture of 0.656 g (4.2 mmoles) of 2, 0.320 g (3.3 mmoles) of trimethylamine hydrochloride, and 2.0 ml of anhydrous methanol was stirred at room temperature for 3 days. The mixture was precipitated into ethyl ether. The product was extracted with water and lyophilized to obtain final product 3.

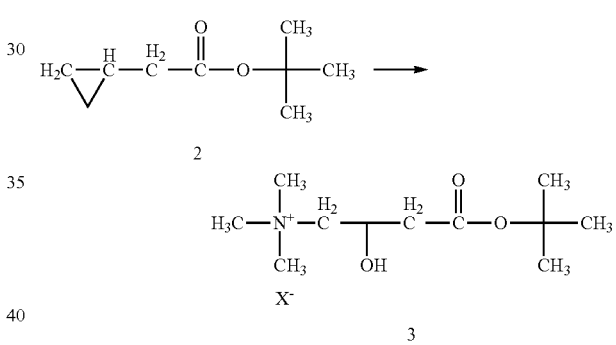

X is the counter ion associated with the cationic center (e.g., halides such as Cl⁻, Br⁻, and I⁻)

Step 3—Synthesis of Acrylic Carnitine tert-butyrate (carnitine-tBu monomer) (4) from Carnitine tert-butyrate (3)

To a solution of 0.218 g (1 mmoles) acrylic carnitine tert-butyrate 3 and 278 µL (2 mmoles) triethylamine in 3 ml of DMF, 161 µL (2 mmoles) of acryloyl chloride in 1 ml DMF solution was added dropwise with ice bath. Then the reaction was continued 2 hours at 40°. Precipitate the mixture in ethyl ether and wash with chloroform for 3 times. Carnitine-tBu monomer was obtained after dried under vacuum.

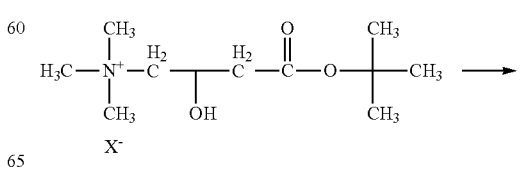

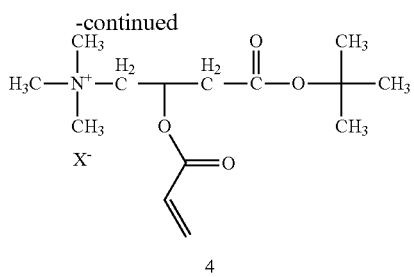

4

Synthesis and Purification of NHS Ester Terminated Carnitine t-Bu Ester Polymer Synthesis of NHS Ester ATRP Initiator N-hydroxysuccinimide (2.26 g) and 1.45 mL of 2-bromopropionic acid were dissolved in 500 ml of anhydrous dichloromethane. The mixture was cooled to 0° C. and a solution of 3.35 g N,N'-dicyclohexylcarbodiimide in 25 mL dichloromethane was added dropwise. After stirring overnight at room temperature, the reaction mixture was filtered and the solvent was removed under reduced pressure to give a yellow solid. The product was further purified by flash chromatography; 2.4 g of NHS ester ATRP initiator (N-hydroxysuccinimide 2-bromopropanoate) was obtained as a white solid (yield=59%)

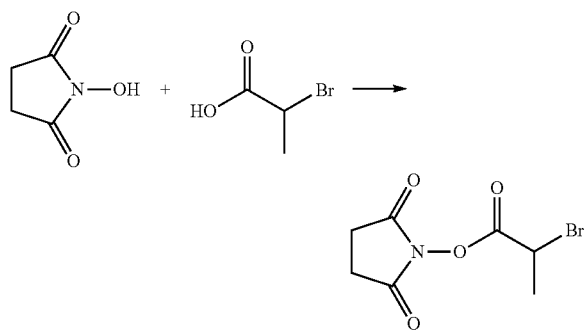

Synthesis of NHS Ester Terminated Carnitine t-Bu Ester Polymer.

Atom transfer radical polymerization (ATRP) of carnitine-tBu monomer was carried out in anhydrous dimethylformamide (DMF) using a Cu(I)Br/1,1,4,7,10,10-hexamethyltriethylenetetramine (HMTETA) catalyst. In a typical polymerization, DMF and the liquid HMTETA ligand were separately purged of oxygen by bubbling with nitrogen. One gram of carnitine-tBu monomer and 118 mg of N-hydroxysuccinimide (NHS) ester ATRP initiator were added to a Schlenk tube. To a second Schlenk tube was added 68 mg of Cu(I)Br. Both tubes were deoxygenated by cycling between nitrogen and vacuum three times. Eight milliliters and 2 mL of deoxygenated DMF were added to the monomer/initiator and Cu(I)Br tubes, respectively; 129 μL of deoxygenated HMTETA was added to the Cu(I)Br containing solution and was stirred for 30 min under nitrogen protection. The catalyst solution (Cu(I)/HMTETA) was then transferred to the monomer/initiator solution to start the reaction. The reaction ran 12 hours at room temperature. After the polymerization, the reaction mixture was fully precipitated in ethyl ether. The precipitate was then dried under vacuum, redissolved in 3-5 mL DMF and precipitated in acetone to remove the soluble catalyst and trace monomers. This dissolve-precipitation cycle was repeated 3 times to fully remove the catalyst. The remaining ester polymer was dried overnight under vacuum and analyzed by NMR.

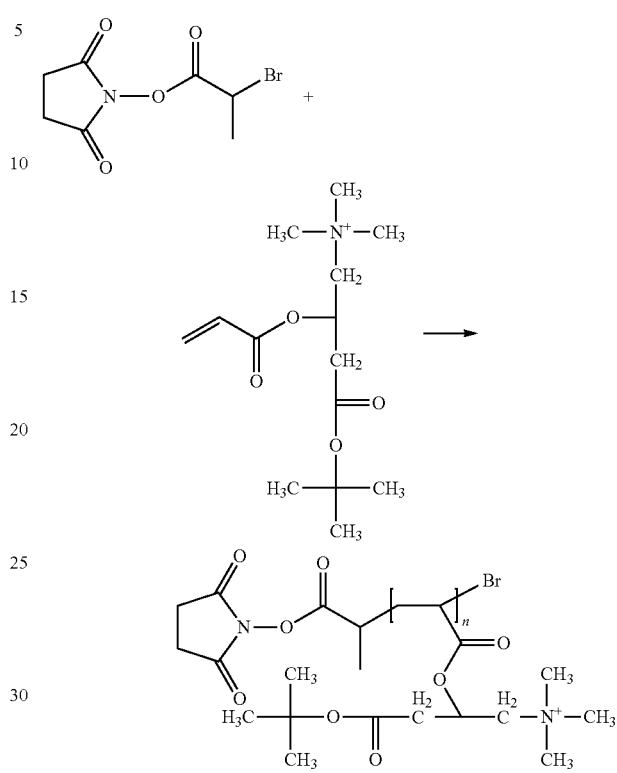

Synthesis and Purification of NH$_2$ Terminated Carnitine t-Bu Ester Polymer Synthesis of NH$_2$ Terminated ATRP Initiator The ATRP initiator with NH$_2$ functional groups were synthesized via a modified method based on established procedures reported previously. Briefly, 3.57 g 2-bromoisobutyryl bromide was added to a solution of 2.5 g t-Boc-aminoethyl alcohol and 1.73 g triethylamine in 8 ml methylene chloride in an ice bath. After 4 h reaction, the salts were filtered off and the filtrate was extracted with saturated sodium bicarbonate solution. Methylene chloride phase was dried over magnesium sulfate and evaporated. The resulting t-Boc-aminoethyl 2-bromoisobutyrate was treated by 15 ml trifluoroacetic acid (TFA) for 2 h and crystallized upon addition of ethyl ether.

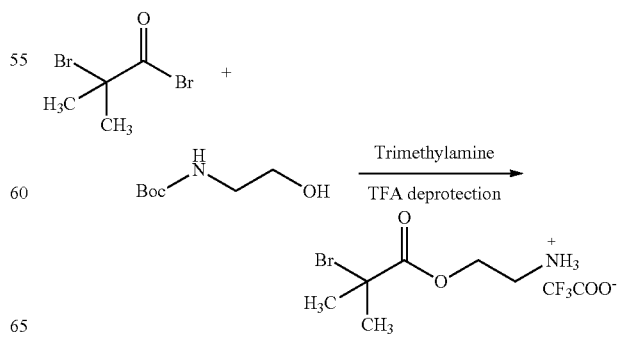

Synthesis of NH$_2$ Terminated Carnitine t-Bu Ester Polymer

The ATRP of carnitine-tBu monomers was carried out as follows: 74 mg Cu(I)Br and 148.6 mg HMTETA were placed into a Schlenk tube and underwent three vacuum-nitrogen cycles. Then, 7 ml degassed DMF was added to make solution A. Similarly, 1.9 g carnitine-tBu monomers and 80 mg 2-aminoethyl 2-bromoisobutyrate were placed into another Schlenk tube with oxygen fully excluded, followed by addition of 8 ml degassed DMF to make solution B. Polymerization was started by transferring solution B into solution A under N$_2$ protection. After reaction at 60° C. for 24 h, the polymers were first precipitated in ethyl ether, then were dissolved in a small amount of ethanol and precipitated in acetone repeatedly to remove residual monomers, initiators and catalysts. TFA-NH$_3^+$ terminated polymer was treated with an excess of triethylamine to remove TFA protection. The resulting NH$_2$ terminated carnitine t-Bu ester polymer was obtained via precipitating into ethyl ether and dried under vacuum before further use.

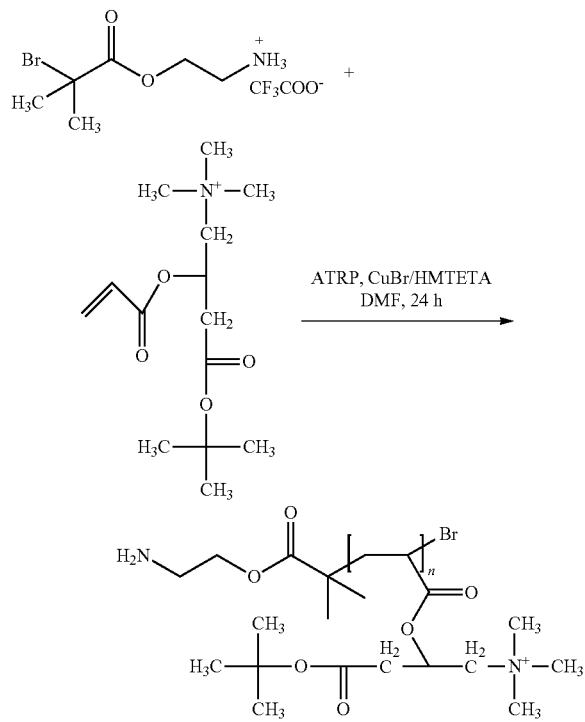

Item List

Item 1. A carnitine-derived zwitterionic monomer having the structural formula (I), where M is a monomeric repeating unit, L1 is a linker, X– is a counter ion associated with a cationic center of structure (I) and Y+ is a counter ion associated with an anionic center of structure (I).

Item 2. The carnitine-derived zwitterionic monomer of item 1, where M is a repeating unit of a polymer selected from the group consisting of: polyester, polyamide, poly(amino acid), polyimide, polycarbonate, polysiloxane, polyurethane, polyphosphazene, acrylic polymer, amino resin, epoxy resin, phenolic resin, and alkyd resin.

Item 3. The carnitine-derived zwitterionic monomer of item 1 or 2 wherein L$_1$ is —C(=O)O—(CH$_2$)$_{n1}$— or —C(=O)NH—(CH$_2$)$_{n1}$—, where n is an integer from 1 to 20, such as where n1 is 3.

Item 4. The carnitine-derived zwitterionic monomer of any one of items 1 to 3, having the structural formula II, where R$_1$ is selected from the group consisting of: hydrogen, fluorine, trifluoromethyl, C$_1$-C$_6$ alkyl, and C$_6$-C$_{12}$ aryl groups, X– is a counter ion associated with the cationic center of structure (II) and Y+ is a counter ion associated with the anion center of structure (II).

Item 5. The carnitine-derived zwitterionic monomer of any one of items 1 to 4, having the structural formula IIa, where X– is a counter ion associated with the cationic center of structure (IIa) and Y+ is a counter ion associated with the anion center of structure (IIa).

Item 6. A carnitine-derived zwitterionic polymer having the structural formula (IV), where M is a monomeric repeating unit, L1 is a linker, n is an integer from 1 to about 10000, X– is a counter ion associated with the cationic center, and Y+ is a counter ion associated with the anionic center.

Item 7. The carnitine-derived zwitterionic polymer of item 6, where M is a repeating unit of a polymer selected from the group consisting of: polyester, polyamide, poly(amino acid), polyimide, polycarbonate, polysiloxane, polyurethane, polyphosphazene, acrylic polymer, amino resin, epoxy resin, phenolic resin, and alkyd resin.

Item 8. The carnitine-derived zwitterionic polymer of item 6 or 7 wherein L$_1$ is —C(=O)O—(CH$_2$)$_{n1}$— or —C(=O)NH—(CH$_2$)$_{n1}$—, where n1 is an integer from 1 to 20, such as where n1 is 3.

Item 9. The carnitine-derived zwitterionic polymer of any one of items 6 to 8, having the structural formula V, where R$_1$ is selected from the group consisting of hydrogen, fluorine, trifluoromethyl, C1-C6 alkyl, and C$_6$-C$_{12}$ aryl groups, n is an integer from 1 to about 10000, X– is a counter ion associated with the cationic center, and Y+ is a counter ion associated with the anionic center.

Item 10. The carnitine-derived zwitterionic polymer of any one of items 6 to 9, having the structural formula Va, where n is an integer from 1 to about 10000, X– is a counter ion associated with the cationic center, and Y+ is a counter ion associated with the anionic center.

Item 11. A carnitine ester cationic monomer having the structural formula (VII), where M is a monomeric repeating unit, L$_1$ is a linker, X– is a counter ion associated with the cationic center, and Z is an alkyl, aryl, acyl, silyl group, or a substituted alkyl, aryl, acyl, or silyl group.

Item 12. A carnitine ester cationic monomer having the structural formula (VIII), where M is a monomeric repeating unit, L1 is a linker, X– is a counter ion associated with the cationic center, and Z1 is a protecting group.

Item 13. A carnitine ester cationic polymer having the structural formula (XVI), where M is a monomeric repeating unit, L1 is a linker, n is an integer from 1 to about 10000, X– is a counter ion associated with the cationic center, and Z is an alkyl, aryl, acyl, silyl group, or a substituted alkyl, aryl, acyl, or silyl group.

Item 14. A carnitine ester cationic polymer having the structural formula (XVII), where M is a monomeric repeating unit, n is an integer from 1 to about 10000, X– is a counter ion associated with the cationic center, and Z1 is a protecting group.

Item 15. A method of synthesizing a carnitine-derived zwitterionic monomer having the structural formula (I) comprising: combining carnitine or a carnitine salt, hydroquinone and anhydrous dimethylformamide in a reaction vessel purged with nitrogen producing a mixture; heating the mixture to a temperature in the range of 40° C. to 60° C., for a time in the range of 5 minutes to 1 hour, producing a first heated mixture; adding acryloyl chloride to the first heated mixture; heating the first heated mixture to a temperature in the range of 70° C. to 90° C., producing a second heated mixture; absorbing excess HCl from the second heated mixture while reacting the second heated mixture at a temperature in the range of 70° C. to 90° C., for a reaction time in the range of 1 to 5 hours, producing a carnitine-derived zwitterionic monomer having the structural formula (I).

Item 16. The method of item 15, wherein the carnitine is L-carnitine and the carnitine salt is an L-carnitine salt.

Item 17. The method of item 15 or 16, wherein the carnitine or carnitine salt has a concentration in the range of about 0.01-2 mol/L in dimethylformamide.

Item 18. The method of any one of items 15, 16, or 17, wherein the molar ratio of the carnitine or carnitine salt to acryloyl chloride is in the range from about 20:1 to 1:20.

Item 19. The method of any one of items 15 to 18, wherein the molar ratio of hydroquinone to acryloyl chloride is in the range of about 1:1 to 1:2000.

Item 20. The method of any one of items 15 to 19, further comprising purification of the carnitine-derived zwitterionic monomer.

Item 21. A composition comprising a carnitine-derived polymer wherein the polymer has structural formula (XXV), where M is a monomeric repeating unit, L1 is a linker, n is an integer from 1 to about 10000, X– is a counter ion associated with the cationic center, and Y+ is a counter ion associated with the anionic center.

Item 22. A composition comprising a carnitine-derived polymer wherein the polymer has structural formula (XXVII), where M is a monomeric repeating unit, L1 is a linker, n is an integer from 1 to about 10000, X– is a counter ion associated with the cationic center, and Y+ is a counter ion associated with the anionic center.

Item 23. A conjugate composition comprising a carnitine-derived zwitterionic polymer covalently coupled to a therapeutic and/or diagnostic agent, wherein the carnitine-derived zwitterionic polymer has structural formula (IV).

Item 24. The conjugate composition of item 23 wherein the carnitine-derived zwitterionic polymer is covalently coupled to a therapeutic and/or diagnostic agent by a degradable linkage between the polymer and the therapeutic or diagnostic agent, and wherein the carnitine-derived zwitterionic polymer has structural formula (IV).

Item 25. The conjugate composition according to item 24, wherein the degradable linkage between the polymer and the therapeutic or diagnostic agent is degradable, allowing the release of the agent in a particular environment.

Item 26. The conjugate composition of any one of items 23, 24, or 25 wherein the conjugate composition comprises a plurality of conjugates, and wherein the plurality of conjugates are associated to form an assembly.

Item 27. The conjugate composition of item 26, wherein the assembly is in the form of a micelle or a particle.

Item 28. The composition of any one of items 23 to 27, further comprising a pharmaceutically accepted carrier or diluent Item 29. A conjugate composition comprising a carnitine-derived zwitterionic polymer covalently coupled to a vesicle-forming lipid, wherein the carnitine-derived zwitterionic polymer has the structural formula (IV).

Item 30. The conjugate composition of item 29, wherein the lipid is distearoylphosphatidylethanolamine (DSEP), and wherein the conjugate composition has the structural formula (XXVI), where M is a monomeric repeating unit, L1 is a linker, n is an integer from 1 to about 10000, X– is a counter ion associated with the cationic center, and Y+ is a counter ion associated with the anionic center.

Item 31. The conjugate composition of item 30, wherein the lipid is a phospholipid, a sphingolipid, or a sterol.

Item 32. The conjugate composition of item 30, wherein the lipid is a diacylphosphatidylethanolamine, a ceramide, a sphingomyelin, a dihydrosphingomyelin, a cephalin, or a cerebroside.

Item 33. The conjugate composition of item 30, wherein the lipid is a phosphatidylethanolamine (PE), a phosphatidylglycerol (PG), aphosphatidic acid (PA), or a phosphatidylinositol (PI).

Item 34. The conjugate composition of item 30, wherein the lipid is selected from the group consisting of dioleoylphosphatidylglycerol (DOPG), dipalmitoylphosphatidylglycerol (DPPG), dioleoyl-phosphatidylethanolamine (DOPE), palmitoyloleoyl-phosphatidylethanolamine (POPE), dipalmitoyl phosphatidyl ethanolamine (DPPE), dimyristoylphosphoethanolamine (DMPE), distearoyl-phosphatidylethanolamine (DSPE), 16-O-monomethyl-phosphoethanolamine, 16-O-dimethyl-phosphoethanolamine, 18-1-trans-phosphoethanolamine, I-stearoyl-2-oleoyl-phosphatidyethanolamine (SOPE), and 1,2-dioleoyl-sn-glycero-3-phophoethanolamine (transDOPE).

Item 35. An assembly, comprising a plurality of conjugates of any one of items 30 to 34.

Item 36. The assembly of item 35 wherein the assembly is in the form of a micelle, a liposome, or a polymersome.

Item 37. The assembly of item 35 or 36, further comprising a pharmaceutically accepted carrier or diluent.

Item 38. The assembly of any one of items 35, 36, or 37, further comprising a therapeutic and/or diagnostic agent.

Item 39. A diblock copolymer, comprising (a) a carnitine-derived zwitterionic polymer block according to structural formula (IV), and (b) a non-zwitterionic block.

Item 40. The diblock copolymer of item 39, wherein the non-zwitterionic block is a hydrophobic block.

Item 41. The diblock copolymer of item 39 or 40, wherein the non-zwitterionic block comprises a homopolymer or copolymer.

Item 42. The diblock copolymer of any one of items 39, 40, or 41, wherein the non-zwitterionic block comprises a biodegradable copolymer.

Item 43. The diblock copolymer of any one of items 40 to 42, wherein the non-zwitterionic block comprises a polymer selected from the group consisting of poly(lactic-co-glycolic acid), polycaprolactone, polyglycolide, polylactic acid, poly-3-hydroxybutyrate, polydioxanone, polytrimethylenecarbonate, poly(glycolide-co-caprolactone), poly(glycolide-co-trimethylenecarbonate), and poly(dioxanon-co-trimethylenecarbonate-co-glycolide).

Item 44. The diblock copolymer of any one of items 39 to 43, wherein the non-zwitterionic block comprises a polymer selected from poly(lactic-co-glycolic acid) (PLGA), poly-(Hydroxyethyl)methacrylate (HEMA), poly-acrylamide (PAA), polyethylene glycol (PEG), alginate, polycaprolactone (PCL), polyglycolide (PG), polylactic acid (PLA), poly-3-hydroxybutyrate, polydioxanone, polytrimethylenecarbonate, poly(glycolide-co-caprolactone) (Monocryl™), poly(glycolide-co-trimethylenecarbonate) (Maxon™), and poly(dioxanon-co-trimethylenecarbonate-co-glycolide) (BioSyn™).

Item 45. The diblock copolymer of any one of items 39 to 44, wherein the hydrophobic block has a number average molecular weight from about 1,000 to about 200,000.

Item 46. An assembly, comprising a plurality of diblock copolymers of any one of items 39 to 45.

Item 47. The assembly of item 46 in the form of a micelle, a polymersome, or a particle.

Item 48. The assembly of item 46 or 47, further comprising a pharmaceutically acceptable carrier or diluent.

Item 49. The assembly of any one of items 46 to 48, further comprising a therapeutic and/or diagnostic agent.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A carnitine-derived zwitterionic monomer having the structural formula (I):

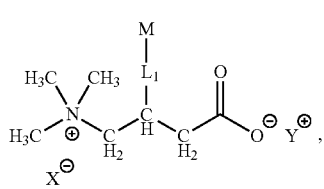

(I)

where M is a monomeric repeating unit, $L_1$ is a linker, X− is a counter ion associated with a cationic center of structure (I) and Y+ is a counter ion selected from the group consisting of: a metal ion, ammonium ion, and an organic ion, wherein Y+ is associated with an anionic center of structure (I).

2. The carnitine-derived zwitterionic monomer of claim 1, where M is a repeating unit of a polymer selected from the group consisting of: polyester, polyamide, poly(amino acid), polyimide, polycarbonate, polysiloxane, polyurethane, polyphosphazene, acrylic polymer, amino resin, epoxy resin, phenolic resin, and alkyd resin.

3. The carnitine-derived zwitterionic monomer of claim 1 wherein L1 is —C(=O)O—$(CH_2)_{n1}$— or —C(=O)NH—$(CH_2)_{n1}$—, where n1 is an integer from 1 to 20.

4. The carnitine-derived zwitterionic monomer of claim 1, having the structural formula II:

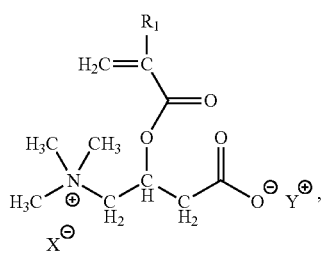

(II)

where $R_1$ is selected from the group consisting of: hydrogen, fluorine, trifluoromethyl, $C_1$-$C_6$ alkyl, and $C_6$-$C_{12}$ aryl groups, X− is a counter ion associated with the cationic center of structure (II) and Y+ is a counter ion associated with the anion center of structure (II).

5. The carnitine-derived zwitterionic monomer of claim 1, having the structural formula IIa:

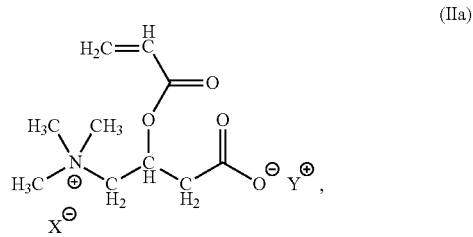

(IIa)

where X− is a counter ion associated with the cationic center of structure (IIa) and Y+ is a counter ion selected from the group consisting of: a metal ion, ammonium ion, and an organic ion, wherein Y+ is associated with the anion center of structure (IIa).

6. A carnitine-derived zwitterionic polymer having the structural formula (IV):

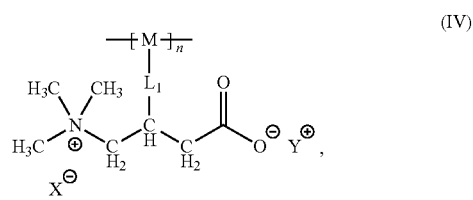

(IV)

where M is a monomeric repeating unit, $L_1$ is a linker, n is an integer from 1 to about 10000, $X^−$ is a counter ion associated with the cationic center, and $Y^+$ is a counter ion associated with the anionic center.

7. The carnitine-derived zwitterionic polymer of claim 6, where M is a repeating unit of a polymer selected from the group consisting of: polyester, polyamide, poly(amino acid), polyimide, polycarbonate, polysiloxane, polyurethane, polyphosphazene, acrylic polymer, amino resin, epoxy resin, phenolic resin, and alkyd resin.

8. The carnitine-derived zwitterionic polymer of claim 6 wherein L1 is —C(=O)O—$(CH_2)_{n1}$— or —C(=O)NH—$(CH_2)_{n1}$—, where n1 is an integer from 1 to 20.

9. The carnitine-derived zwitterionic polymer of claim 6, having the structural formula V:

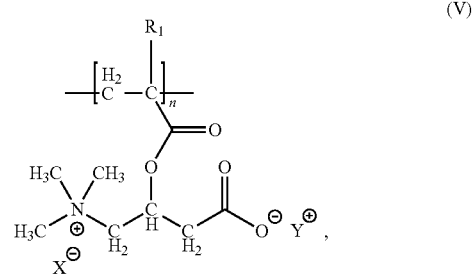

(V)

where $R_1$ is selected from the group consisting of hydrogen, fluorine, trifluoromethyl, $C_1$-$C_6$ alkyl, and $C_6$-$C_{12}$ aryl groups, n is an integer from 1 to about 10000, $X^−$ is a counter ion associated with the cationic center, and $Y^+$ is a counter ion associated with the anionic center.

10. The carnitine-derived zwitterionic polymer of claim 6, having the structural formula Va:

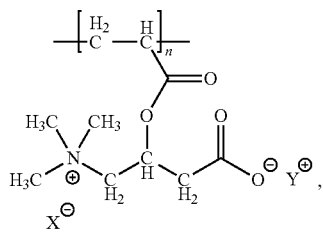

(Va)

where n is an integer from 1 to about 10000, $X^-$ is a counter ion associated with the cationic center, and $Y^+$ is a counter ion associated with the anionic center.

11. A conjugate composition comprising a carnitine-derived zwitterionic polymer covalently coupled to a therapeutic and/or diagnostic agent, wherein the carnitine-derived zwitterionic polymer has structural formula

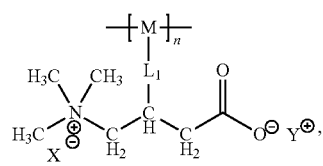

(IV)

where M is a monomeric repeating unit, $L_1$ is a linker, n is an integer from 1 to about 10000, $X^-$ is a counter ion associated with the cationic center, and $Y^+$ is a counter ion associated with the anionic center,

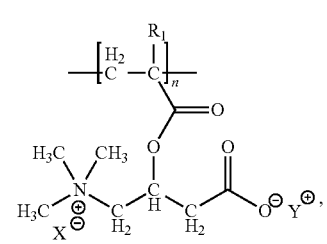

(V)

where $R_1$ is selected from the group consisting of hydrogen, fluorine, trifluoromethyl, $C_1$-$C_6$ alkyl, and $C_6$-$C_{12}$ aryl groups, n is an integer from 1 to about 10000, $X^-$ is a counter ion associated with the cationic center, and $Y^+$ is a counter ion associated with the anionic center, or

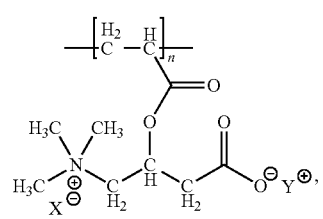

(Va)

where n is an integer from 1 to about 10000, $X^-$ is a counter ion associated with the cationic center, and $Y^+$ is a counter ion associated with the anionic center.

12. The conjugate composition of claim 11 wherein the carnitine-derived zwitterionic polymer is covalently coupled to a therapeutic and/or diagnostic agent by a degradable linkage between the polymer and the therapeutic or diagnostic agent, and wherein the carnitine-derived zwitterionic polymer has structural formula

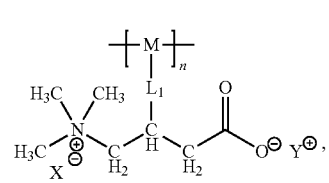

(IV)

where M is a monomeric repeating unit, $L_1$ is a linker, n is an integer from 1 to about 10000, $X^-$ is a counter ion associated with the cationic center, and $Y^+$ is a counter ion associated with the anionic center,

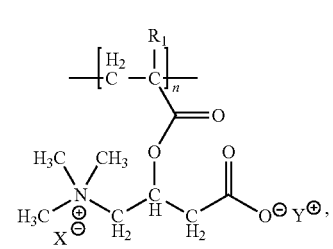

(V)

where $R_1$ is selected from the group consisting of hydrogen, fluorine, trifluoromethyl, $C_1$-$C_6$ alkyl, and $C_6$-$C_{12}$ aryl groups, n is an integer from 1 to about 10000, $X^-$ is a counter ion associated with the cationic center, and $Y^+$ is a counter ion associated with the anionic center, or

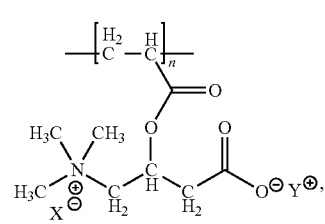

(Va)

where n is an integer from 1 to about 10000, $X^-$ is a counter ion associated with the cationic center, and $Y^+$ is a counter ion associated with the anionic center.

13. A conjugate composition comprising a carnitine-derived zwitterionic polymer covalently coupled to a vesicle-forming lipid, wherein the carnitine-derived zwitterionic polymer has the structural formula (IV)

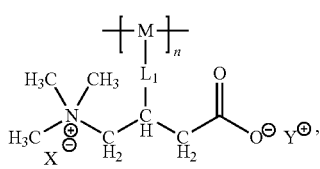

where M is a monomeric repeating unit, $L_1$ is a linker, n is an integer from 1 to about 10000, X− is a counter ion associated with the cationic center, and $Y^+$ is a counter ion associated with the anionic center, (V)

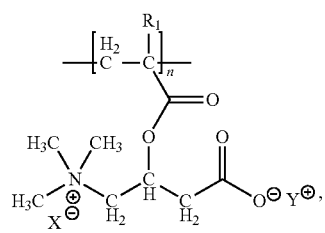

where $R_1$ is selected from the group consisting of hydrogen, fluorine, trifluoromethyl, $C_1$-$C_6$ alkyl, and $C_6$-$C_{12}$ aryl groups, n is an integer from 1 to about 10000, $X^-$ is a counter ion associated with the cationic center, and $Y^+$ is a counter ion associated with the anionic center, or (Va)

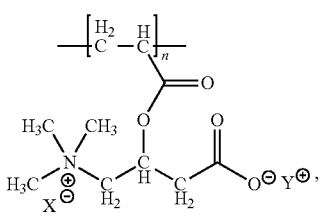

where n is an integer from 1 to about 10000, $X^-$ is a counter ion associated with the cationic center, and $Y^+$ is a counter ion associated with the anionic center.

14. The conjugate composition of claim 13, wherein the lipid is distearoylphosphatidylethanolamine (DSEP), and wherein the conjugate composition has the structural formula (XXVI)

where M is a monomeric repeating unit, $L_1$ is a linker, n is an integer from 1 to about 10000, $X^-$ is a counter ion associated with the cationic center, and $Y^+$ is a counter ion associated with the anionic center.

15. An assembly, comprising a plurality of conjugates of claim 14.

16. The assembly of claim 15 wherein the assembly is in the form of a micelle, a liposome, or a polymersome.

17. The assembly of claim 15, further comprising a therapeutic and/or diagnostic agent.

18. A diblock copolymer, comprising (a) a carnitine-derived zwitterionic polymer block according to structural formula (IV)

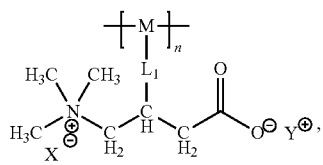

where M is a monomeric repeating unit, $L_1$ is a linker, n is an integer from 1 to about 10000, $X^-$ is a counter ion associated with the cationic center, and $Y^+$ is a counter ion associated with the anionic center, (V)

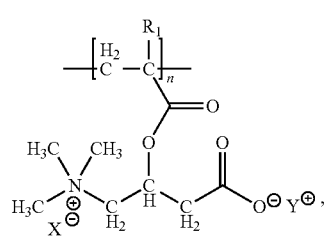

where $R_1$ is selected from the group consisting of hydrogen, fluorine, trifluoromethyl, $C_1$-$C_6$ alkyl, and $C_6$-$C_{12}$ aryl groups, n is an integer from 1 to about 10000, $X^-$ is a counter ion associated with the cationic center, and $Y^+$ is a counter ion associated with the anionic center, or (XXVI)

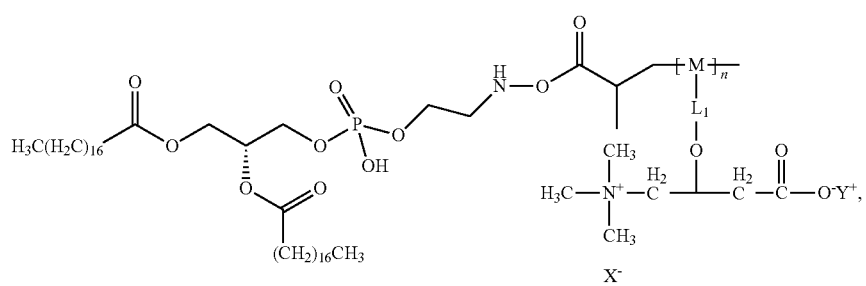

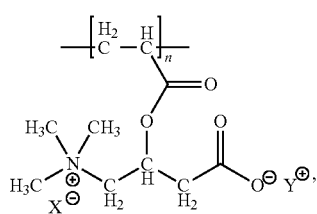

(Va)

where n is an integer from 1 to about 10000, X− is a counter ion associated with the cationic center, and Y+ is a counter ion associated with the anionic center, and (b) a non-zwitterionic block.

19. The diblock copolymer of claim 18, wherein the non-zwitterionic block is a hydrophobic block.

20. The diblock copolymer of claim 18, wherein the non-zwitterionic block comprises a homopolymer.

21. The diblock copolymer of claim 18, wherein the non-zwitterionic block comprises a biodegradable copolymer.

22. The diblock copolymer of claim 19, wherein the non-zwitterionic block comprises a polymer selected from the group consisting of poly(lactic-co-glycolic acid), polycaprolactone, polyglycolide, polylactic acid, poly-3-hydroxybutyrate, polydioxanone, polytrimethylenecarbonate, poly(glycolide-co-caprolactone), poly(glycolide-co-trimethylenecarbonate), and poly(dioxanon-co-trimethylenecarbonate-co-glycolide).

23. The diblock copolymer of claim 18, wherein the non-zwitterionic block comprises a polymer selected from poly(lactic-co-glycolic acid) (PLGA), poly-(Hydroxyethyl) methacrylate (HEMA), poly-acrylamide (PAA), polyethylene glycol (PEG), alginate, polycaprolactone (PCL), polyglycolide (PG), polylactic acid (PLA), poly-3-hydroxybutyrate, polydioxanone, polytrimethylenecarbonate, poly(glycolide-co-caprolactone), poly(glycolide-co-trimethylenecarbonate), and poly(dioxanon-co-trimethylenecarbonate-co-glycolide).

24. The diblock copolymer of claim 19, wherein the hydrophobic block has a number average molecular weight from about 1,000 to about 200,000.

25. An assembly, comprising a plurality of diblock copolymers of claim 18.

26. The assembly of claim 25 in the form of a micelle, a polymersome, or a particle.

27. The diblock copolymer of claim 18, wherein the non-zwitterionic block comprises a copolymer.

* * * * *